(12) United States Patent
Li et al.

(10) Patent No.: US 11,939,350 B2
(45) Date of Patent: *Mar. 26, 2024

(54) FLUORESCENT DYES AND METHODS OF USE THEREOF

(71) Applicant: ENZO LIFE SCIENCES, INC., Farmingdale, NY (US)

(72) Inventors: Zaiguo Li, Little Neck, NY (US); Praveen Pande, Holbrook, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 509 days.

This patent is subject to a terminal disclaimer.

(21) Appl. No.: 16/952,399

(22) Filed: Nov. 19, 2020

(65) Prior Publication Data

US 2021/0079034 A1 Mar. 18, 2021

Related U.S. Application Data

(60) Continuation of application No. 16/127,950, filed on Sep. 11, 2018, now Pat. No. 10,875,886, which is a continuation of application No. 15/205,438, filed on Jul. 8, 2016, now Pat. No. 10,106,573, which is a division of application No. 13/270,456, filed on Oct. 11, 2011, now Pat. No. 9,416,153.

(51) Int. Cl.
| | |
|---|---|
| C09B 11/24 | (2006.01) |
| C07H 19/04 | (2006.01) |
| C07H 21/00 | (2006.01) |
| C09B 11/02 | (2006.01) |
| C09B 11/06 | (2006.01) |
| C12Q 1/70 | (2006.01) |

(52) U.S. Cl.
CPC ............ *C07H 21/00* (2013.01); *C07H 19/04* (2013.01); *C09B 11/02* (2013.01); *C09B 11/06* (2013.01); *C09B 11/24* (2013.01); *C12Q 1/707* (2013.01)

(58) Field of Classification Search
CPC ......... C07H 21/00; C07H 19/04; C09B 11/02; C09B 11/06; C09B 11/24; C12Q 1/707; C12Q 2563/107
See application file for complete search history.

(56) References Cited

U.S. PATENT DOCUMENTS

| | | |
|---|---|---|
| 4,683,202 A | 7/1987 | Mullis |
| 4,711,955 A | 12/1987 | Ward et al. |
| 4,868,103 A | 9/1989 | Stavrianopoulos et al. |
| 4,952,685 A | 8/1990 | Stavrianopoulos |
| 5,013,831 A | 5/1991 | Stavrianopoulos |
| 5,047,519 A | 9/1991 | Hobbs, Jr. et al. |
| 5,118,801 A | 6/1992 | Lizardi et al. |
| 5,130,238 A | 7/1992 | Malek et al. |
| 5,210,015 A | 5/1993 | Gelfand et al. |
| 5,237,515 A | 8/1993 | Herron |
| 5,241,060 A | 8/1993 | Engelhardt et al. |
| 5,268,486 A | 12/1993 | Waggoner et al. |
| 5,270,184 A | 12/1993 | Walker et al. |
| 5,401,847 A | 3/1995 | Glazer et al. |
| 5,455,166 A | 10/1995 | Walker |
| 5,455,175 A | 10/1995 | Wittwer et al. |
| 5,494,810 A | 2/1996 | Barany et al. |
| 5,538,848 A | 7/1996 | Livak et al. |
| 5,580,990 A | 12/1996 | van den Berg et al. |

(Continued)

FOREIGN PATENT DOCUMENTS

| | | |
|---|---|---|
| EE | 0971039 | 1/2000 |
| EP | 0070685 | 1/1983 |

(Continued)

OTHER PUBLICATIONS

Ernst et al. Cyanine Dye Labeling Reagents for Sulfhydryl Groups, Cytometry 1989, 3-10, 10.

(Continued)

*Primary Examiner* — Jezia Riley
(74) *Attorney, Agent, or Firm* — Quarles & Brady LLP

(57) ABSTRACT

Provided are methods for labeling target molecules, such as nucleic acids, with fluorescent dye compounds having the formula

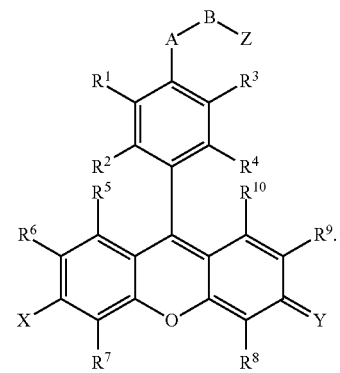

One method embodiment includes contacting reactive group Z of the fluorescent dye compound with the target molecule such that reactive group Z reacts with the target molecule to form a covalent bond between the group and the target molecule. Another method embodiment includes contacting a fluorescent dye compound that further includes a first member of a binding pair, with a target molecule that includes a second member of the binding pair. Also provided are target molecules labeled with the fluorescent dye compounds.

20 Claims, 4 Drawing Sheets

Specification includes a Sequence Listing.

(56) References Cited

U.S. PATENT DOCUMENTS

| | | |
|---|---|---|
| 5,627,027 A | 5/1997 | Waggoner |
| 5,646,264 A | 7/1997 | Glazer et al. |
| 5,800,996 A | 9/1998 | Lee et al. |
| 5,866,336 A | 2/1999 | Nazarenko et al. |
| 5,925,517 A | 7/1999 | Tyagi et al. |
| 5,948,648 A | 9/1999 | Khan et al. |
| 5,994,056 A | 11/1999 | Higuchi |
| 6,004,286 A | 12/1999 | Bellhouse et al. |
| 6,008,373 A | 12/1999 | Waggoner et al. |
| 6,110,630 A | 8/2000 | Reddy et al. |
| 6,114,350 A | 9/2000 | Randall et al. |
| 6,117,635 A | 9/2000 | Nazarenko et al. |
| 6,166,202 A | 12/2000 | Simmonds et al. |
| 6,174,670 B1 | 1/2001 | Wittwer et al. |
| 6,184,379 B1 | 2/2001 | Josel et al. |
| 6,323,337 B1 | 11/2001 | Singer et al. |
| 6,552,199 B1 | 4/2003 | Daltrozzo et al. |
| 6,593,465 B1 | 7/2003 | Wolff et al. |
| 6,743,605 B1 | 6/2004 | Rabbani et al. |
| 7,432,298 B2 | 10/2008 | Lam et al. |
| 10,106,573 B2 * | 10/2018 | Li ................ C07D 311/88 |
| 2003/0055257 A1 | 3/2003 | Lee et al. |
| 2003/0225247 A1 | 12/2003 | Stavrianopoulos et al. |
| 2005/0042618 A1 | 2/2005 | Heindl et al. |
| 2005/0137388 A1 | 6/2005 | Rabbani et al. |
| 2005/0176014 A1 | 8/2005 | Heindl et al. |
| 2012/0157385 A1 | 6/2012 | Selwood et al. |

FOREIGN PATENT DOCUMENTS

| | | |
|---|---|---|
| EP | 0543333 | 5/1993 |
| EP | 0567622 | 11/1993 |
| EP | 0971039 | 1/2000 |
| WO | WO93/10189 | 5/1993 |
| WO | WO1993/10189 | 5/1993 |
| WO | WO99/28500 | 6/1999 |
| WO | WO1999/28500 | 6/1999 |
| WO | WO99/47700 | 9/1999 |
| WO | WO1999/47700 | 9/1999 |

OTHER PUBLICATIONS

Mujumdar et al. Cyanine Dye Labeling Reagents: Sulfoindocyanine Succinimidyl Esters, Bioconjugate Chemistry 1993, 105-111, 4.

Mujumdar et al. Cyanine Dye Labeling Reagents Containing Isothiocyanate Groups, Cytometry 1989, 11-19, 10.

Southwick et al. Cyanine Dye Labeling Reagents-Carboxymethylindocyanine Succinimidyl Esters, Cytometry 1990, 418-430, 11.

Zhu et al., Directly labeled DNA probes using fluorescent nucleotides with different length linkers, Nucleic Acids Research, 1994, 3418-3422, 22.

International Search Report of copending application PCT/US13/59285, 1 page.

Kamiya et al., "An Enzymatically Activated Fluorescence Probe for Targeted Tumor Imaging," J. Am. Chem. Soc., vol. 129, pp. 3918-3929 (2007).

Kobayashi et al., "Highly Activatable and Rapidly Releasable Caged Fluorescein Derivatives," j. am. Chem. Soc., vol. 129, pp. 6696-6697 (2007).

Meng et al., "Novel highly selective Fluorescent Chemosensors for Zn(II)," *Tetrahedron Letters*, vol. 47, pp. 1559-1562 (2006).

Sauer et al., "Design of multiplex dyes for the detection of different biomolecule," SPIE, vol. 2137, pp. 762-774 (1994).

Sauer et al., "Design of Multiplex Dyes," Ber. Bunsenges. Phys. Chem., vol. 97, No. 12, pp. 1734-1737 (1993).

Teeuwen et al., "Clickable" elastins: elastin-like polypeptides functionalized with azide or alkyne groups, *Chem. Comm.*, pp. 4022-4024 (2009).

Srikun et al., organelle-Targetable Fluorescent Probes for Imaging Hydrogen Peroxide in Living Cells via SNAP-Tag Protein Labeling, *J. Am. Chem. Soc.*, vol. 132, pp. 4455-4465 (2010).

* cited by examiner

SEQUENCE LISTING

<160> NUMBER OF SEQ ID NOS: 3

<210> SEQ ID NO 1
<211> LENGTH: 57
<212> TYPE: RNA
<213> ORGANISM: Hepatitis C virus

<400> SEQUENCE: 1
gaggaacuac ugucuucacg cagaaagcgu cuagccaugg cguuaguaug agugucg    57

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaggaactac tgtcttcacg cagaaagcg                                   29

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgacactcat actaacgcca tggctag                                     27

FLUORESCENT DYES AND METHODS OF USE THEREOF

CROSS-REFERENCE TO RELATED APPLICATIONS

This application is a continuation of U.S. application Ser. No. 16/127,950 filed Sep. 11, 2018, which is a continuation of U.S. application Ser. No. 15/205,438 filed Jul. 8, 2016 (now U.S. Pat. No. 10,106,573), which is a divisional of U.S. application Ser. No. 13/270,456 filed Oct. 11, 2011 (now U.S. Pat. No. 9,416,153), each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 8, 2016, is named ENZ-100-D1-SL.txt and is 869 bytes in size.

FIELD OF THE INVENTION

The present application generally relates to fluorescent dyes. More specifically, the invention is directed to rhodamine and fluorescein dyes useful for labeling nucleic acids and other molecules.

BACKGROUND OF THE INVENTION

Numerous rhodamine and fluorescein dyes are available that are useful for labeling nucleic acids, proteins and other molecules. See, e.g., U.S. Pat. Nos. 6,184,379 and 6,552,199; European Patent Publications 0 543 333 and 0 567 622, and references cited therein.

Labeling methods for attaching rhodamine and fluorescein dyes and other non-radioactive compounds to various molecules are well developed. Non-radioactive labeling methods were initially developed to attach signal-generating groups onto proteins. This was achieved by modifying labels with chemical groups such that they would be capable of reacting with the amine, thiol, and hydroxyl groups that are naturally present on proteins. Examples of reactive groups that were used for this purpose include activated esters such as N-hydroxysuccinimide esters, isothiocyanates and other compounds. Consequently, when it became desirable to label nucleotides and nucleic acids by non-radioactive means, methods were developed to convert nucleotides and polynucleotides into a form that made them functionally similar to proteins. For instance, U.S. Pat. No. 4,711,955 discloses the addition of amines to the 8-position of a purine, the 5-position of a pyrimidine and the 7-position of a deazapurine. The same methods that could add a label to the amine group of a protein could thus be applied towards these modified nucleotides.

Dyes have been synthesized with arms containing functional groups with iodoacetamide, isothiocyanate or succinimidyl esters that react with sulfhydryl groups on proteins (Ernst et al., 1989; Mujumdar, et al., 1989; Southwick, et al., 1990). Another series of modified dyes contain a sulfonate group on the phenyl portion of an indolenine ring that increased the water solubility of the dyes (Mujumdar et al., 1993). Those dyes were activated by treatment with disuccinimidyl carbonate to form succinimidyl esters that were then used to label proteins by substitution at the amine groups. Other activating groups have also been placed on dyes. U.S. Pat. Nos. 5,627,027 and 5,268,486 describe dyes which comprise isothiocyanate, isocyanate, monochlorotriazine, dichlorotriazine, mono or di-halogen substituted pyridine, mono or di-halogen substituted diazine, aziridine, sulfonyl halide, acid halide, hydroxy-succinimide ester, hydroxy-sulfosuccinimide ester, imido esters, glyoxal groups, aldehydes or other groups, all of which can form a covalent bond with an amine, thiol or hydroxyl group on a target molecule.

U.S. Pat. No. 6,110,630 describes cyanine dyes prepared with a series of reactive groups derived from N-hydroxynaphthalimide. These groups include hydroxysuccinimide, para-nitrophenol, N-hydroxyphtalimide and N-hydroxynaphtalimide, all of which can react with nucleotides modified with primary amines. The same chemical reactions described above were also described in U.S. Pat. No. 6,114,350 where the constituents where reversed. There, the cyanine dyes were modified with amine, sulfhydryl or hydroxyl groups and the target molecules were modified to comprise the appropriate reactive groups.

Labeled nucleotides have been used for the synthesis of DNA and RNA probes in many enzymatic methods including terminal transferase labeling, nick translation, random priming, reverse transcription, RNA transcription and primer extension. Labeled phosphoramidite versions of these nucleotides have also been used with automated synthesizers to prepare labeled oligonucleotides. The resulting labeled probes are widely used in such standard procedures as northern blotting, Southern blotting, in situ hybridization, RNAse protection assays, DNA sequencing reactions, DNA and RNA microarray analysis and chromosome painting.

There is an extensive literature on chemical modification of nucleic acids by means of which a signal moiety is directly or indirectly attached to a nucleic acid. Primary concerns of this art have been (a) which site in a nucleic acid is used for attachment, i.e. sugar, base or phosphate or analogues thereof, and whether these sites are disruptive or non-disruptive (see, e.g., U.S. Pat. Nos. 4,711,955 and 5,241,060); (b) the chemistry at the site of attachment that allows linkage to a reactive group or signaling moiety that can comprise a spacer group usually consisting of a single aromatic group (U.S. Pat. Nos. 4,952,685 and 5,013,831) or a carbon/carbon aliphatic chain to provide distance between the nucleic acid and the reactive group or signaling moiety and a reactive group at the end of the spacer, such as an OH, NH, SH or some other group that can allow coupling to a signaling moiety; and (c) the nature of the signaling moiety.

Although the foregoing have all been descriptions of the various aspects that are concerned with the synthesis of modified nucleotides and polynucleotides, they have also been shown to be significant factors with regard to the properties of the resultant nucleotides and polynucleotides. Indeed, there have been numerous demonstrations that the modified nucleotides described in the present art have shortcomings compared to unmodified nucleotides. These factors can have a major impact on the ability of these modified nucleotides to be incorporated by polymerases. A consequence of this is that when using a modified base as the sole source of that particular nucleotide, there may be a loss in the amount of nucleic acid synthesis compared to a reaction with unmodified nucleotides. As a result, modified nucleotides are often employed as part of a mixture of modified and unmodified versions of a given nucleotide. Although this restores synthesis to levels comparable to reactions without any modified nucleotides, a bias is often seen against the use of the modified version of the nucleotide. As such, the final proportion of modified/unmodified nucleotide may be much lower than the ratio of the reagents at the beginning of the reaction. Users then have a choice of either using nucleic acids that are minimally labeled or of decreased yields. When comparable modified nucleotides are used that only comprise a linker arm attached to a base (such as allylamine dUTP) difficulties with incorporation are seldom seen. As such, the foregoing problem is likely to be due to the interactions of the label with either the polymerase or the active site where synthesis is taking place.

Difficulties in the use of polymerases can be bypassed by the use of oligonucleotide synthesizers where an ordered chemical joining of e.g., phosphoramidite derivatives of nucleotides can be used to produce labeled nucleic acids of interest. However, the presence of signal agents on modified nucleotides can still be problematic in this system. For instance, a phosphoramidite of a modified nucleotide may display a loss of coupling efficiency as the chain is extended. Although this may be problematic in itself, multiple and especially successive use of modified nucleotides in a sequence for a synthetic oligonucleotide can result in a drastic cumulative loss of product. Additionally, chemical synthesis is in itself not always an appropriate solution. There may be circumstances where labeled nucleic acids need to be of larger lengths than is practical for a synthesizer. Also, an intrinsic part of synthetic approaches is a necessity for a discrete sequence for the nucleic acid. For many purposes, a pool or library of nucleic acids would require an impractically large number of different species for synthetic approaches.

An example of a method to increase the yield of labeled oligonucleotides or polynucleotide is to use a non-interfering group such as an allylamine modified analogue during synthesis by either a polymerase or an oligonucleotide synthesizer. Labeling is then carried out post-synthetically by attachment of the desired group through the chemically reactive allylamine moieties. However, in this case, although incorporation or coupling efficiency may be restored, there may still be problems of the coupling efficiencies of attachment of the desired group to the allylamine. For instance, coupling of labels to allylamine moieties in a nucleic acid is dramatically less efficient for double-stranded DNA compared to single-stranded targets. In addition to potential yield problems, the functionality of the modification may be affected by how it is attached to a base. For instance if a hapten is attached to a base, the nature of the arm separating the hapten from the base may affect its accessibility to a potential binding partner. When a signal generating moiety is attached through a base, the nature of the arm may also affect interactions between the signal generating moiety and the nucleotide and polynucleotide.

Attempts to limit these deleterious interactions have been carried out in several ways. For instance, attachment of the arm to the base has been carried out with either a double bond alkene group (U.S. Pat. No. 4,711,955) or a triple bond alkyne group (U.S. Pat. No. 5,047,519) thereby inducing a directionality of the linker away from the nucleotide or polynucleotide. In addition, deleterious interactions can be limited by having the arm displace the active or signal group away from the nucleotide or polynucleotide by lengthening the spacer group. For instance, a commercially available modified nucleotide includes a seven carbon aliphatic chain (Cat. No. 42724, ENZO Biochem, Inc. New York, NY) between the base and a biotin moiety used for signal generation. This product was further improved by the substitution of linkers with 11 or even 16 carbon lengths (Cat. Nos. 42722 and 42723, ENZO Biochem, Inc. New York, NY). A comparison was also carried out using different length linker arms and a cyanine dye labeled nucleotide (Zhu et al., 1994). A direct improvement in efficiency was noted as the length was increased from 10 to 17 and from 17 to 24.

Another approach was taken in U.S. Pat. No. 5,948,648, which describes the use of multiple alkyne or aromatic groups connecting a marker to a nucleotide.

It is noted that the above-described difficulties do not occur with the use of polymerases with labeled probes (e.g., labeled phosphoramidite probes), where the probes are extended along a template using unmodified nucleotides or derivatives, since the polymerase does not encounter the label-modified nucleotide during the extension reaction. Thus, probes that are utilized in extension reactions and are synthesized chemically can employ a greater variety of conjugation methods and linkers than oligonucleotides or polynucleotides that are labeled enzymatically.

Amplification of nucleic acids from clinical samples has become a widely used technique. The first methodology for this process, the Polymerase Chain Reaction (PCR), is described in U.S. Pat. No. 4,683,202. Since that time, other methodologies such as Ligation Chain Reaction (LCR) (U.S. Pat. No. 5,494,810), GAP-LCR (U.S. Pat. No. 6,004, 286), Nucleic Acid Sequence Based Amplification (NASBA) (U.S. Pat. No. 5,130,238), Strand Displacement Amplification (SDA) (U.S. Pat. Nos. 5,270,184 and 5,455, 166) and Loop Mediated Amplification (U.S. Pat. No. 6,743, 605; European Patent Publication 0 971 039) have been described. Detection of an amplified product derived from the appropriate target has been carried out in number of ways. In PCR as described in U.S. Pat. No. 4,683,202, gel analysis was used to detect the presence of a discrete nucleic acid species. Identification of this species as being indicative of the presence of the intended target was determined by size assessment and the use of negative controls lacking the target sequence. The placement of the primers used for amplification dictated a specific size for the product from appropriate target sequence. Spurious amplification products made from non-target sequences were unlikely to have the same size product as the target derived sequence. Alternatively, more elaborate methods have been used to examine the particular nature of the sequences that are present in the amplification product. For instance, restriction enzyme digestion has been used to determine the presence, absence or spatial location of specific sequences. The presence of the appropriate sequences has also been established by hybridization experiments. In this method, the amplification product can be used as either the target or as a probe.

The foregoing detection methods have historically been used after the amplification reaction was completed. More recently, methods have been described for measuring the extent of synthesis during the course of amplification, i.e. "real-time" detection. For instance, in the simplest system, an intercalating agent is present during the amplification reaction (U.S. Pat. Nos. 5,994,056 and 6,174,670). This method takes advantage of an enhancement of fluorescence exhibited by the binding of an intercalator to double-stranded nucleic acids. Measurement of the amount of fluorescence can take place post-synthetically in a fluorometer after the reaction is over, or real time measurements can be carried out during the course of the reaction by using a PCR cycler machine that is equipped with a fluorescence detection system and uses capillary tubes for the reactions (U.S. Pat. Nos. 5,455,175 and 6,174,670). As the amount of double-stranded material rises during the course of amplification, the amount of signal also increases. The sensitivity of this system depends upon a sufficient amount of double-stranded nucleic acid being produced to generate a signal that is distinguishable from the fluorescence of a) unbound intercalator and b) intercalator molecules bound to single-stranded primers in the reaction mix. Specificity is derived from the nature of the amplification reaction itself or by looking at a $T_m$ profile of the reaction products. Although the initial work was done with ethidium bromide, SYBR Green™ is more commonly used at the present time. A variation of this system is described in U.S. Pat. No. 6,323,337, where the primers used in PCR reactions were modified with quenchers thereby reducing signal generation of a fluorescent intercalator that was bound to a primer dimer molecule. Signal generation from target derived amplicons could still take place since amplicons derived from target sequences comprised intercalators bound to segments that were sufficiently distant from the quenchers.

Another method of analysis that depends upon incorporation is described in U.S. Pat. No. 5,866,336. In that system, signal generation is dependent upon the incorporation of primers into double-stranded amplification products. The primers are designed such that they have extra sequences added onto their 5' ends. In the absence of amplification, stem-loop structures are formed through intramolecular hybridization that consequently bring an energy transfer (FRET) quencher into proximity with an energy donor thereby preventing fluorescence. However, when a primer becomes incorporated into double-stranded amplicons, the quencher and donor become physically separated and the donor is then able to produce a fluorescent signal. The specificity of this system depends upon the specificity of the amplification reaction itself. Since the stem-loop sequences are derived from extra sequences, the $T_m$ profile of signal generation is the same whether the amplicons were derived from the appropriate target molecules or from non-target sequences.

In addition to incorporation based assays, probe based systems can also be used for real-time analysis. For instance, a dual probe system can be used in a homogeneous assay to detect the presence of appropriate target sequences. In this method, one probe comprises an energy donor and the other probe comprises an energy acceptor (European Patent Publication 0 070 685). Thus, when the target sequence is present, the two probes can bind to adjacent sequences and allow energy transfer to take place. In the absence of target sequences, the probes remain unbound and no energy transfer takes place. Even if by chance there are non-target sequences in a sample that are sufficiently homologous that binding of one or both probes takes place, no signal is generated since energy transfer requires that both probes bind and that they be in a particular proximity to each other. Advantage of this system has been taken in U.S. Pat. No. 6,174,670 for real time detection of PCR amplification using the capillary tube equipped PCR machine described previously. The primer annealing step during each individual cycle can also allow the simultaneous binding of each probe to target sequences providing an assessment of the presence and amount of the target sequences. In a further refinement of this method, one of the primers comprises an energy transfer element and a single energy transfer probe is used. Labeled probes have also been used in conjunction with fluorescent intercalators to allow the specificity of the probe methodology to be combined with the enhancement of fluorescence derived from binding to nucleic acids. This was first described in U.S. Pat. No. 4,868,103 and later described with amplification reactions in PCT Publication WO 99/28500.

Probes have also been used that comprise an energy donor and an energy acceptor in the same nucleic acid. In these assays, the energy acceptor "quenches" fluorescent energy emission in the absence of appropriate complementary targets. In one system described in U.S. Pat. No. 5,118,801, "molecular beacons" are used where the energy donor and the quencher are kept in proximity by secondary structures with internal base pairing. When the target sequences are present, complementary sequences in the molecular beacons allow hybridization events that destroy the secondary structure thereby allowing energy emission. In another system that has been termed Taqman, use is made of the double-stranded selectivity of the exonuclease activity of Taq polymerase (U.S. Pat. No. 5,210,015). When target molecules are present, hybridization of the probe to complementary sequences converts the single-stranded probe into a substrate for the exonuclease. Degradation of the probe separates an energy transfer donor from the quencher thereby releasing light from the donor.

U.S. Patent Publication 2005/0137388 also describes various formats for utilization of FRET interactions for various nucleic acid assays.

Because fluorescent dyes are used widely, e.g., for labeling nucleic acids, proteins and other molecules, there is an ongoing need for new dyes to provide more options for labeling methods and linker arm selections, spectral profiles and energy transfer (FRET) pair selection. The present invention addresses that need.

SUMMARY OF THE INVENTION

In some embodiments, compounds are provided that comprise:

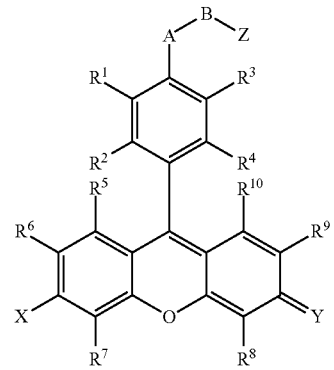

wherein
$R^1$, $R^2$, $R^3$, $R^4$, $R^5$, $R^6$, $R^7$, $R^8$, $R^9$, and $R^{10}$ are independently H, F, Cl, Br, I, CN, nitro, azido, hydroxyl, amino, hydrazino, (substituted) aryl, (substituted) aroxyl, alkenyl, alkynyl, alkyl, alkoxy, alkylamino, dialkylamino, arylamino, diarylamino, alkyl(aryl)amino, alkanoylamino, alkylthio, alkylcarbonyl, aryl carbonyl, alkylthiocarbonyl, arylthiocarbonyl, alkyloxycarbonyl, aroxycarbonyl, alkylaminocarbonyl, arylaminocarbonyl, dialkylaminocarbonyl, diarylaminocarbonyl, alkyl(aryl)aminocarbonyl, arylcarboxamido, or Q, the alkyl or alkoxy portions of which are saturated or unsaturated, linear or branched, unsubstituted or further substituted by F, Cl, Br, I, CN, OH, alkenyl, alkynyl, alkylcarbonyl, amide, thioamide, or Q; wherein Q comprises a carboxyl group ($CO_2^-$), a carbonate ester (COER$^{11}$), a sulfonate ester (SO$_2$ER$^{11}$), a sulfoxide (SOR$^{11}$), a sulfone (SO$_2$CR$^{11}$R$^{12}$R$^{13}$), a sulfonamide (SO$_2$NR$^{11}$R$^{12}$), a phosphate (PO$_4^-$), a phosphate monoester (PO$_3^-$ER$^{11}$), a phosphate diester (PO$_2$ER$^{11}$ER$^{12}$), a phosphonate (PO$_3^-$), a phosphonate monoester (PO$_2^-$ER$^{11}$), a phosphonate diester (POER$^{11}$ER$^{12}$), a thiophosphate (PSO$_3^-$), a thiophosphate monoester (PSO$_2^-$ER$^{11}$), a thiophosphate diester (PSOER$^{11}$ER$^{12}$), a thiophosphonate (PSO$_2^-$), a thiophosphonate monoester (PSO$^-$ER$^{11}$), a thiophosphonate diester (PSER$^{11}$ER$^{12}$), a phosphonamide (PONR$^{11}$R$^{12}$NR$^{14}$R$^{15}$), a phosphonamide thioanalogue (PSNR$^{11}$R$^{12}$NR$^{14}$R$^{15}$), a phosphoramide (PONR$^{11}$R$^{12}$NR$^{13}$NR$^{14}$R$^{15}$), a phosphoramide thioanalogue (PSNR$^{11}$R$^{12}$NR$^{13}$NR$^{14}$R$^{15}$), a phosphoramidite (PO$_2$R$^{14}$NR$^{11}$R$^{12}$) or a phosphoramidite thioanalogue (POSR$^{14}$NR$^{11}$R$^{12}$), where E can be independently O or S, and where the aryl portions of any of the above are optionally substituted by F, Cl, Br, I, CN, OH, alkenyl, alkynyl, alkylcarbonyl, amide, or thioamide;

wherein R$^1$ in combination with R$^2$, R$^3$ in combination with R$^4$, R$^5$ in combination with R$^6$, or R$^9$ in combination with R$^{10}$ can independently form a 5-10 member ring structure which is saturated or unsaturated, and which is optionally further substituted with an alkyl, an aryl, an alkenyl, an alkynyl, an alkoxy, an aroxyl, a hydroxyl, an F, a Cl, a Br, an I, a CN, a nitro, an alkylsulfonyl, an arylsulfonyl, an alkylsulfinyl, an arylsulfinyl, a (thio)carbonyl, a (thio)carboxylic acid, a (thio)carboxylic acid ester, a nitro, an amino, a (thio)amide, an azido, a hydrazino, or a (thio)phosphonate where each alkyl group or alkoxy group is independently saturated or unsaturated, linear or branched, or substituted or unsubstituted and each aryl group wherein is independently optionally substituted with an F, a Cl, a Br, an I, a CN, an OH, an alkyl, an alkenyl, an alkynyl, an alkoxy, an aryoxy, an alkylthio, an arylthio, a nitro, an azido, a hydrazino, a carboxyl, a thiocarboxyl, a carbonyl, a thiocarbonyl, a carboxylic acid ester, a thiocarboxylic acid ester, or an unsubstituted or substituted amino, amide, thioamide, or Q;

R$^{11}$, R$^{12}$, R$^{13}$, R$^{14}$ and R$^{15}$ are independently a hydrogen, a halogen, an amino group, an alkyl group wherein said alkyl group is saturated or unsaturated, linear or branched, or substituted or unsubstituted, an alkoxy group wherein said alkoxy group is saturated or unsaturated, branched or linear, or substituted or unsubstituted, an aryl group wherein said aryl group is unsubstituted or substituted; wherein R$^{11}$ in combination with R$^{12}$, R$^{14}$ in combination with R$^{15}$, R$^{11}$ in combination with R$^{13}$, R$^{11}$ in combination with R$^{14}$, R$^{12}$ in combination with R$^{15}$, or R$^{13}$ in combination with R$^{14}$ can independently form a 5-10 member ring;

X is O, OR$^{16}$, NR$^{17}$R$^{18}$ or N$^+$R$^{17}$R$^{18}$; Y is O, OR$^{16}$, NR$^{19}$R$^{20}$ or N$^+$R$^{19}$R$^{20}$, wherein R$^{16}$, R$^{17}$, R$^{18}$, R$^{19}$ and R$^{20}$ are independently H, alkyl, alkenyl, alkynyl, or aryl; or R$^{17}$ in combination with R$^{18}$, or R$^{19}$ in combination with R$^{20}$ can independently form a 5-10 member ring structure which is optionally further substituted with alkyl, alkenyl, alkynyl, aryl, alkoxy, F, Cl, Br, I, carboxylic acid or carboxylic acid ester, where the alkyl group is saturated or unsaturated, linear or branched, and is optionally further substituted by F, Cl, Br, I, CN, OH, alkenyl, alkynyl, nitro, azido, hydrazino, alkoxy, aryoxy, alkylthio, arylthio, thiocarboxyl, carbonyl, thiocarbonyl, thiocarboxylic acid ester, unsubstituted or substituted amino, amide, thioamide, or Q, and the aryl group wherein is optionally substituted by F, Cl, Br, I, CN, OH, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, unsubstituted or substituted amino, amide, thioamide, or Q;

wherein R$^{17}$ in combination with R$^6$, R$^{18}$ in combination with R$^7$, R$^{19}$ in combination with R$^8$, or R$^{20}$ in combination with R$^9$, can independently form a 5- to 10-member ring structure that is saturated or unsaturated and optionally further substituted with an alkyl, an aryl, an alkenyl, an alkynyl, an alkoxy, an aroxyl, a hydroxyl, an F, a Cl, a Br, an I, a CN, a nitro, a carbonyl, a thiocarbonyl, a thiocarboxylic acid, a thiocarboxylic acid ester, a nitro, an amino, a (thio)amide, an azido, a hydrazino, or Q, wherein the alkyl group herein is saturated or unsaturated, linear or branched, substituted or unsubstituted, an alkoxy group wherein the alkoxy group is saturated or unsaturated, branched or linear, substituted or unsubstituted; and wherein the aryl group is optionally substituted with F, Cl, Br, I, CN, OH, alkenyl, alkynyl, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, unsubstituted or substituted amino, amide, thioamide, or Q;

A is O, S or NR$^{21}$, wherein R$^{21}$ is a hydrogen, an alkyl, an aryl, an alkenyl, an alkynyl, an alkylcarbonyl, an arylcarbonyl, an alkylaminocarbonyl, or an arylaminocarbonyl, the alkyl or aryl portions of which is optionally substituted by an alkyl, an aryl, an alkenyl, an alkynyl, an F, a Cl, a Br, an I, a CN, an OH, an alkoxy, an aryoxy, an alkylthio, an arylthio, a nitro, an azido, a hydrazino, a thiocarboxyl, a carbonyl, a thiocarbonyl, a thiocarboxylic acid ester, or an unsubstituted or substituted amino, amide, thioamide, or Q;

B is an alkyl, an alkenyl, an alkynyl, or an aryl linker, the alkyl or aryl portions of which is optionally substituted by an alkyl, an alkenyl, an alkynyl, an aryl, an F, a Cl, a Br, an I, a CN, an OH, an alkoxy, an aryoxy, an alkylthio, an arylthio, a nitro, an azido, a hydrazino, a carboxyl, a thiocarboxyl, a carbonyl, a thiocarbonyl, a carboxylic acid ester, a thiocarboxylic acid ester, or an unsubstituted or substituted amino, amide, thioamide, or Q; or B in combination with A form an amide, a thioamide, a carboxylic acid ester, a carboxylic acid thioester, a thiocarboxylic acid ester, an imine, a hyrazone, or Q; and Z is a reactive group comprising an isocyanate, an isothiocyanate, a monochlorotriazine, a dichlorotriazine, a 4,6-dichloro-1,3,5-triazines, a mono- or di-halogen substituted pyridine, a mono- or di-halogen substituted diazine, a maleimide, a haloacetamide, an aziridine, a sulfonyl halide, a carboxylic acid, an acid halide, a phosphonyl halide, a phosphoramidite (PO$_2$R$^{14}$NR$^{11}$R$^{12}$), a phosphoramidite thioanalogue (POSR$^{14}$NR$^{11}$R$^{12}$), a hydroxysuccinimide ester, a hydroxysulfosuccinimide ester, an imido ester, an azido, a nitrophenol ester, an azide, a 3-(2-pyridyl dithio)-propionamide, a glyoxal, an aldehyde, a thiol, an amine, a hydrazine, a hydroxyl, a terminal alkene, a terminal alkyne, a platinum coordinate group or an alkylating agent.

In other embodiments, a fluorescent dye comprising the above compound is provided.

Also provided is a fluorescence energy transfer system, comprising the above-described fluorescent dye and a second dye wherein the second dye is capable of energy transfer with the fluorescent dye.

Further provided is a kit for labeling a target molecule. The kit comprises the above-described fluorescent dye with additional reagents useful for labeling the target molecule.

A target molecule labeled with the above-described fluorescent dye is also provided.

Additionally, a method of labeling a target molecule is provided. The method comprises contacting reactive group Z of the above-described fluorescent dye with the target molecule such that reactive group Z reacts with the target molecule to form a covalent bond between reactive group Z and the target molecule.

Another method of labeling a target molecule is also provided. The method comprises contacting the above-described fluorescent dye, where the fluorescent dye further comprises a first member of a binding pair. In this method, the target molecule comprises a second member of the binding pair.

BRIEF DESCRIPTION OF THE DRAWINGS

FIG. 1A shows the UV-Vis spectra of LC Red 640 and EZRed620.

FIG. 1B shows the emission spectra of LC Red 640 and EZRed620.

FIG. 1C shows the UV-Vis and emission spectra of LC Red 640.

FIG. 1D shows the UV-Vis and emission spectra of EZRed620.

DETAILED DESCRIPTION

Figure 1A:
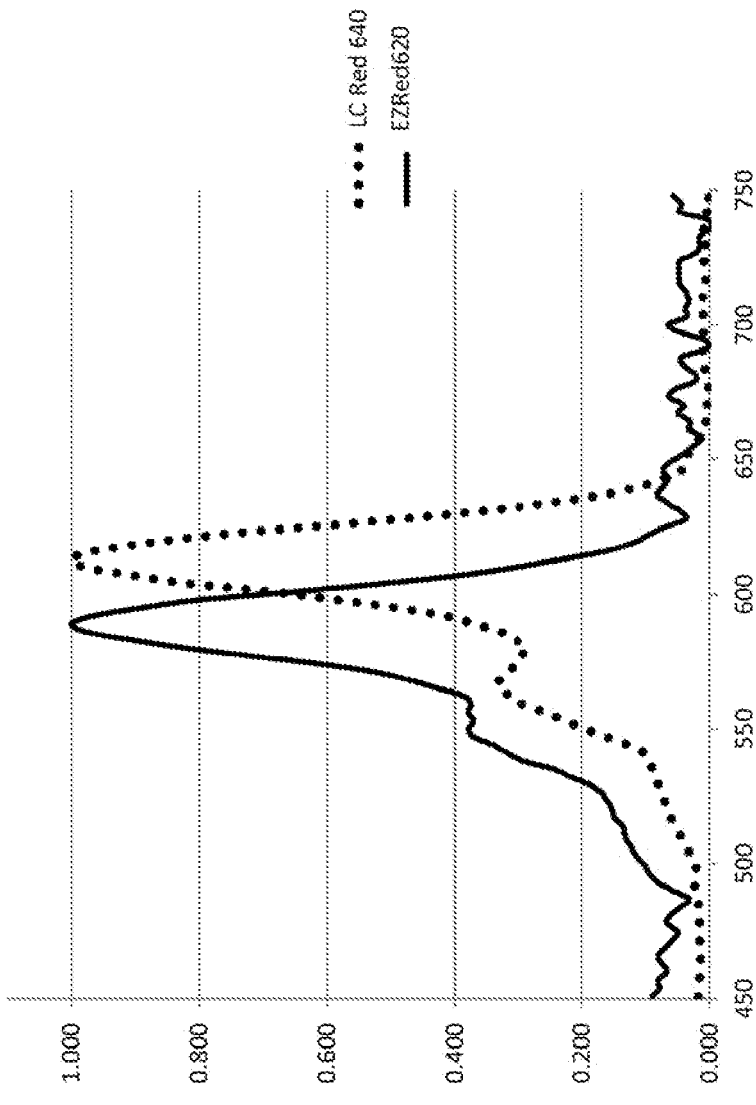
FIGS. 1A-1D are graphs showing spectral properties of Dye 1 (EZRed620) and prior art dye LC Red 640 (Roche).

As used herein, the singular forms "a", "an" and "the" are intended to include the plural forms as well, unless the context clearly indicates otherwise. Additionally, the use of "or" is intended to include "and/or", unless the context clearly indicates otherwise.

Provided herein are novel rhodamine dyes that are useful for, e.g., labeling nucleic acids or other molecules. In some embodiments, the present invention provides a compound comprising:

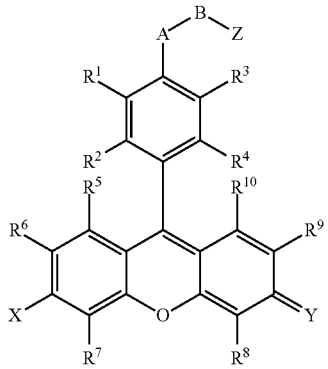

wherein
$R^1$, $R^2$, $R^3$, $R^4$, $R^5$, $R^6$, $R^7$, $R^8$, $R^9$, and $R^{10}$ are independently H, F, Cl, Br, I, CN, nitro, azido, hydroxyl, amino, hydrazino, (substituted) aryl, (substituted) aroxyl, alkenyl, alkynyl, alkyl, alkoxy, alkylamino, dialkylamino, arylamino, diarylamino, alkyl(aryl)amino, alkanoylamino, alkylthio, alkylcarbonyl, aryl carbonyl, alkylthiocarbonyl, arylthiocarbonyl, alkyloxycarbonyl, aroxycarbonyl, alkylaminocarbonyl, arylaminocarbonyl, dialkylaminocarbonyl, diarylaminocarbonyl, alkyl(aryl)aminocarbonyl, arylcarboxamido, or Q, the alkyl or alkoxy portions of which are saturated or unsaturated, linear or branched, unsubstituted or further substituted by F, Cl, Br, I, CN, OH, alkenyl, alkynyl, alkylcarbonyl, amide, thioamide, or Q; wherein Q comprises a carboxyl group ($CO_2^-$), a carbonate ester ($COER^{11}$), a sulfonate ester ($SO_2ER^{11}$), a sulfoxide ($SOR^{11}$), a sulfone ($SO_2CR^{11}R^{12}R^{13}$), a sulfonamide ($SO_2NR^{11}R^{12}$), a phosphate ($PO_4^=$), a phosphate monoester ($PO_3^-ER^{11}$), a phosphate diester ($PO_2ER^{11}ER^{12}$), a phosphonate ($PO_3^=$), a phosphonate monoester ($PO_2^-ER^{11}$), a phosphonate diester ($POER^{11}ER^{12}$), a thiophosphate ($PSO_3^=$), a thiophosphate monoester $PSO_2^-ER^{11}$), a thiophosphate diester ($PSOER^{11}ER^{12}$), a thiophosphonate ($PSO_2^=$), a thiophosphonate monoester ($PSO^-ER^{11}$), a thiophosphonate diester ($PSER^{11}ER^{12}$), a phosphonamide ($PONR^{11}R^{12}NR^{14}R^{15}$), a phosphonamide thioanalogue ($PSNR^{11}R^{12}NR^{14}R^{15}$), a phosphoramide ($PONR^{11}R^{12}NR^{13}NR^{14}R^{15}$), a phosphoramide thioanalogue ($PSNR^{11}R^{12}NR^{13}NR^{14}R^{15}$), a phosphoramidite ($PO_2R^{14}NR^{11}R^{12}$) or a phosphoramidite thioanalogue ($POSR^{14}NR^{11}R^{12}$), where E can be independently O or S, and where the aryl portions of any of the above are optionally substituted by F, Cl, Br, I, CN, OH, alkenyl, alkynyl, alkylcarbonyl, amide, or thioamide;

wherein $R^1$ in combination with $R^2$, $R^3$ in combination with $R^4$, $R^5$ in combination with $R^6$, or $R^9$ in combination with $R^{10}$ can independently form a 5-10 member ring structure which is saturated or unsaturated, and which is optionally further substituted with an alkyl, an aryl, an alkenyl, an alkynyl, an alkoxy, an aroxyl, a hydroxyl, an F, a Cl, a Br, an I, a CN, a nitro, an alkylsulfonyl, an arylsulfonyl, an alkylsulfinyl, an arylsulfinyl, a (thio)carbonyl, a (thio)carboxylic acid, a (thio)carboxylic acid ester, a nitro, an amino, a (thio)amide, an azido, a hydrazino, or a (thio)phosphonate where each alkyl group or alkoxy group is independently saturated or unsaturated, linear or branched, or substituted or unsubstituted and each aryl group wherein is independently optionally substituted with an F, a Cl, a Br, an I, a CN, an OH, an alkyl, an alkenyl, an alkynyl, an alkoxy, an aryoxy, an alkylthio, an arylthio, a nitro, an azido, a hydrazino, a carboxyl, a thiocarboxyl, a carbonyl, a thiocarbonyl, a carboxylic acid ester, a thiocarboxylic acid ester, or an unsubstituted or substituted amino, amide, thioamide, or Q;

$R^{11}$, $R^{12}$, $R^{13}$, $R^{14}$ and $R^{15}$ are independently a hydrogen, a halogen, an amino group, an alkyl group wherein said alkyl group is saturated or unsaturated, linear or branched, or substituted or unsubstituted, an alkoxy group wherein said alkoxy group is saturated or unsaturated, branched or linear, or substituted or unsubstituted, an aryl group wherein said aryl group is unsubstituted or substituted; wherein $R^{11}$ in combination with $R^{12}$, $R^{14}$ in combination with $R^{15}$, $R^{11}$ in combination with $R^{13}$, $R^{11}$ in combination with $R^{14}$, $R^{12}$ in combination with $R^{15}$, or $R^{13}$ in combination with $R^{14}$ can independently form a 5-10 member ring;

X is O, $OR^{16}$, $NR^{17}R^{18}$ or $N^+R^{17}R^{18}$; Y is O, $OR^{16}$, $NR^{19}R^{20}$ or $N^+R^{19}R^{20}$, wherein $R^{16}$, $R^{17}$, $R^{18}$, $R^{19}$ and $R^{20}$ are independently H, alkyl, alkenyl, alkynyl, or aryl; or $R^{17}$ in combination with $R^{18}$, or $R^{19}$ in combination with $R^{20}$ can independently form a 5-10 member ring structure which is optionally further substituted with alkyl, alkenyl, alkynyl, aryl, alkoxy, F, Cl, Br, I, carboxylic acid or carboxylic acid ester, where the alkyl group is saturated or unsaturated, linear or branched, and is optionally further substituted by F, Cl, Br, I, CN, OH, alkenyl, alkynyl, nitro, azido, hydrazino, alkoxy, aryoxy, alkylthio, arylthio, thiocarboxyl, carbonyl, thiocarbonyl, thiocarboxylic acid ester, unsubstituted or substituted amino, amide, thioamide, or Q, and the aryl group wherein is optionally substituted by F, Cl, Br, I, CN, OH, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, unsubstituted or substituted amino, amide, thioamide, or Q;

wherein $R^{17}$ in combination with $R^6$, $R^{18}$ in combination with $R^7$, $R^{19}$ in combination with $R^8$, or $R^{20}$ in combination with $R^9$, can independently form a 5- to 10-member ring structure that is saturated or unsaturated and optionally further substituted with an alkyl, an aryl, an alkenyl, an alkynyl, an alkoxy, an aroxyl, a hydroxyl, an F, a Cl, a Br, an I, a CN, a nitro, a carbonyl, a thiocarbonyl, a thiocarboxylic acid, a thiocarboxylic acid ester, a nitro, an amino, a (thio)amide, an azido, a hydrazino, or Q, wherein the alkyl group herein is saturated or unsaturated, linear or branched, substituted or unsubstituted, an alkoxy group wherein the alkoxy group is saturated or unsaturated, branched or linear, substituted or unsubstituted; and wherein the aryl group is optionally substituted with F, Cl, Br, I, CN, OH, alkenyl, alkynyl, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, unsubstituted or substituted amino, amide, thioamide, or Q;

A is O, S or $NR^{21}$, wherein $R^{21}$ is a hydrogen, an alkyl, an aryl, an alkenyl, an alkynyl, an alkylcarbonyl, an arylcarbonyl, an alkylaminocarbonyl, or an arylaminocarbonyl, the alkyl or aryl portions of which is optionally substituted by an alkyl, an aryl, an alkenyl, an alkynyl, an F, a Cl, a Br, an I, a CN, an OH, an alkoxy, an aryoxy, an alkylthio, an arylthio, a nitro, an azido, a hydrazino, a thiocarboxyl, a carbonyl, a thiocarbonyl, a thiocarboxylic acid ester, or an unsubstituted or substituted amino, amide, thioamide, or Q;

B is an alkyl, an alkenyl, an alkynyl, or an aryl linker, the alkyl or aryl portions of which is optionally substituted by an alkyl, an alkenyl, an alkynyl, an aryl, an F, a Cl, a Br, an I, a CN, an OH, an alkoxy, an aryoxy, an alkylthio, an arylthio, a nitro, an azido, a hydrazino, a carboxyl, a thiocarboxyl, a carbonyl, a thiocarbonyl, a carboxylic acid ester, a thiocarboxylic acid ester, or an unsubstituted or substituted amino, amide, thioamide, or Q; or B in combination with A form an amide, a thioamide, a carboxylic acid ester, a carboxylic acid thioester, a thiocarboxylic acid ester, an imine, a hyrazone, or Q; and Z is a reactive group comprising an isocyanate, an isothiocyanate, a monochlorotriazine, a dichlorotriazine, a 4,6-dichloro-1,3,5-triazines, a mono- or di-halogen substituted pyridine, a mono- or di-halogen substituted diazine, a maleimide, a haloacetamide, an aziridine, a sulfonyl halide, a carboxylic acid, an acid halide, a phosphonyl halide, a phosphoramidite ($PO_2R^{14}NR^{11}R^{12}$), a phosphoramidite thioanalogue ($POSR^{14}NR^{11}R^{12}$), a hydroxysuccinimide ester, a hydroxysulfosuccinimide ester, an imido ester, an azido, a nitrophenol ester, an azide, a 3-(2-pyridyl dithio)-propionamide, a glyoxal, an aldehyde, a thiol, an amine, a hydrazine, a hydroxyl, a terminal alkene, a terminal alkyne, a platinum coordinate group or an alkylating agent.

In some of these embodiments, -A-B—Z is

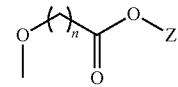

where n is 1-10, i.e., 1, 2, 3, 4, 5, 6, 7, 8, 9 or 10, for example 1-4. In certain of these embodiments, -A-B—Z is

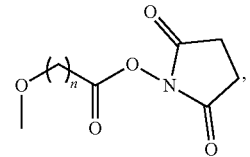

providing a reactive hydroxysuccinimide ester group for coupling to amine moieties, as is known in the art. In more specific embodiments, -A-B—Z is

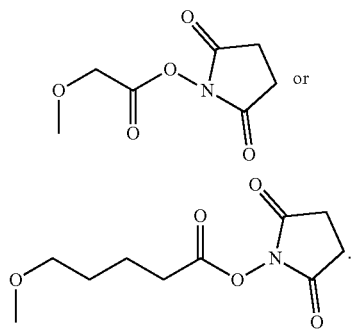

Some compounds of these embodiments comprise

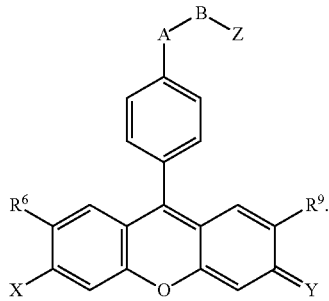

In certain embodiments of those compounds, $R^6$ and $R^9$ are both H, or both $CH_3$. In other embodiments of those compounds, X and Y are (a) OH and O, respectively;

(b) $NHCH_2CH_3$ and $NCH_2CH_3$, respectively; or (c) $N(CH_3)_2$ and $N^+(CH_3)_2$, respectively.

Specific examples of the compounds of these embodiments comprise

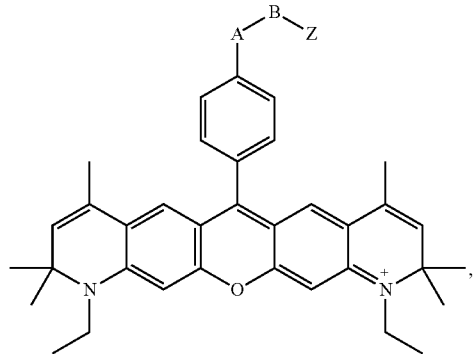

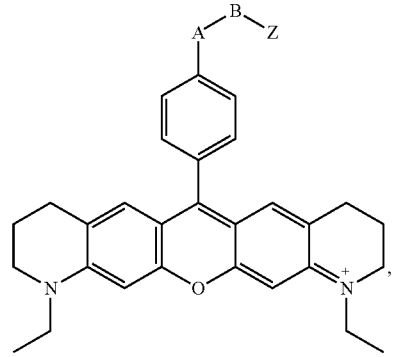

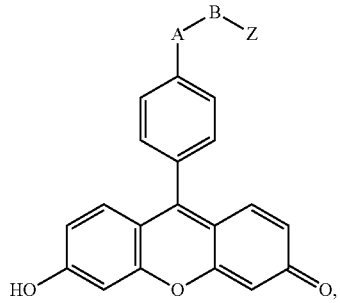

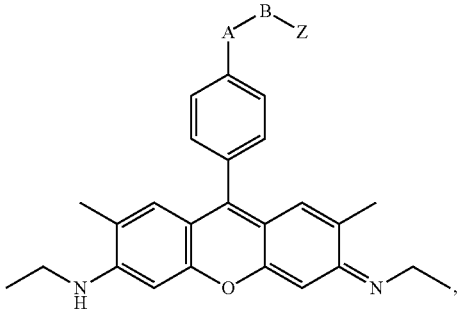

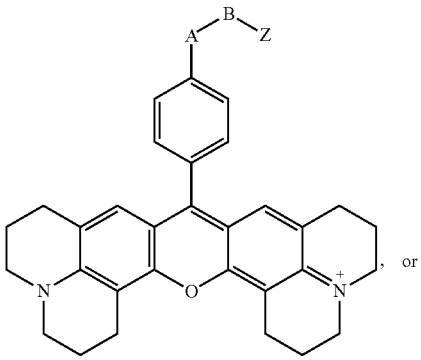

, or

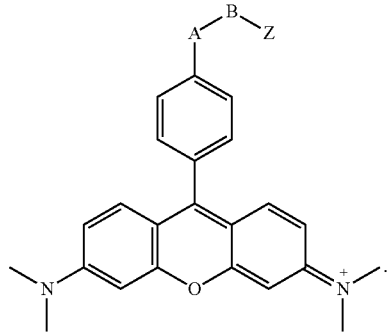

Other specific examples comprise

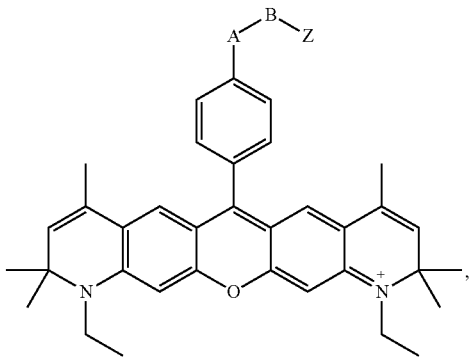

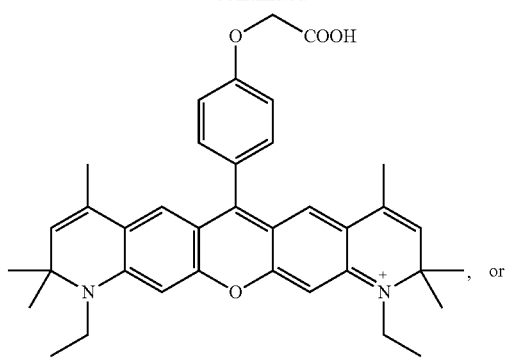
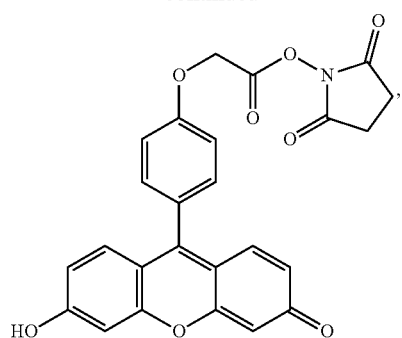
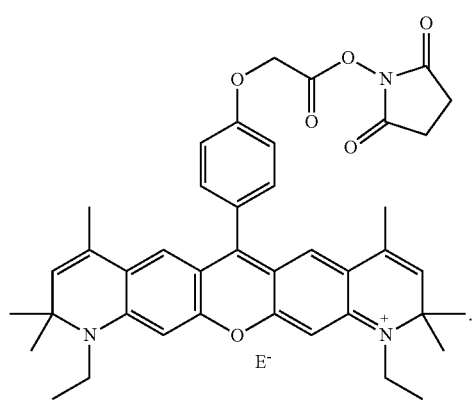
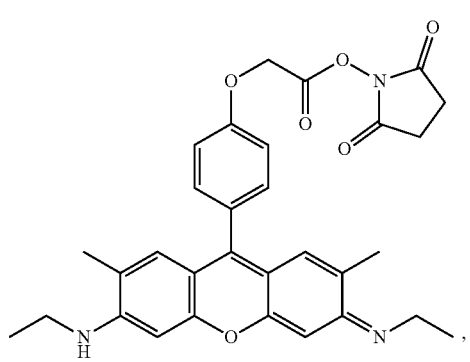
Still other specific examples comprise
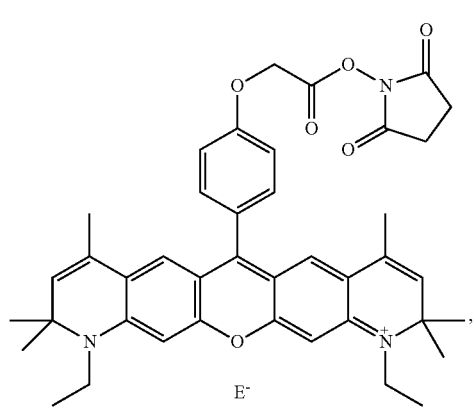
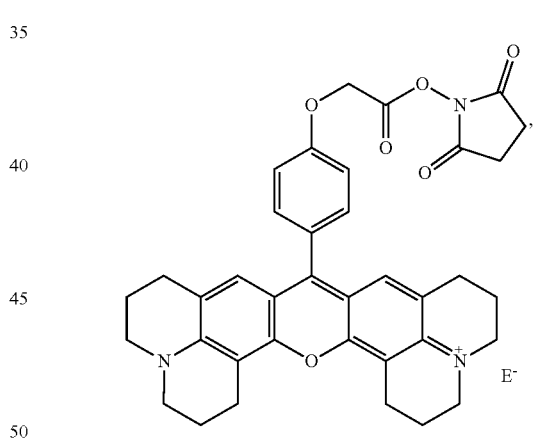
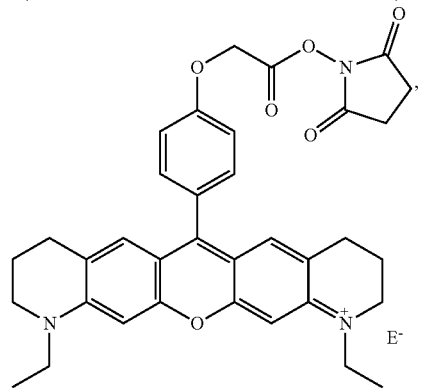
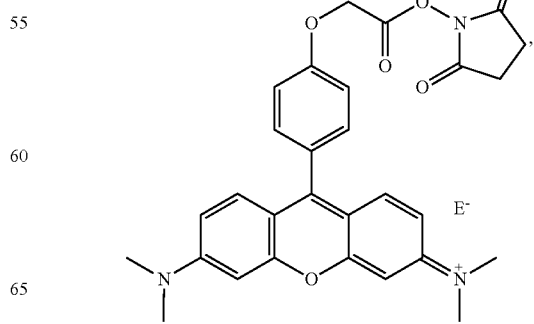

-continued

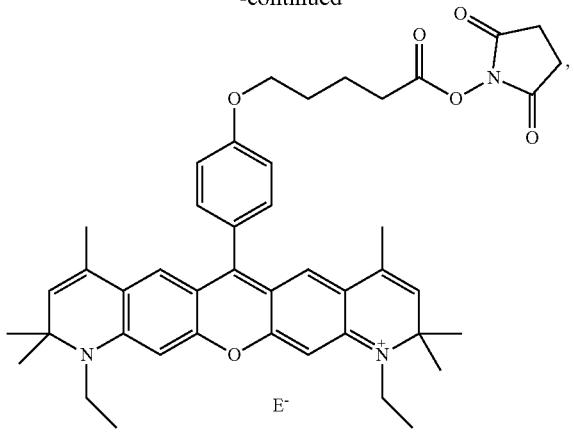

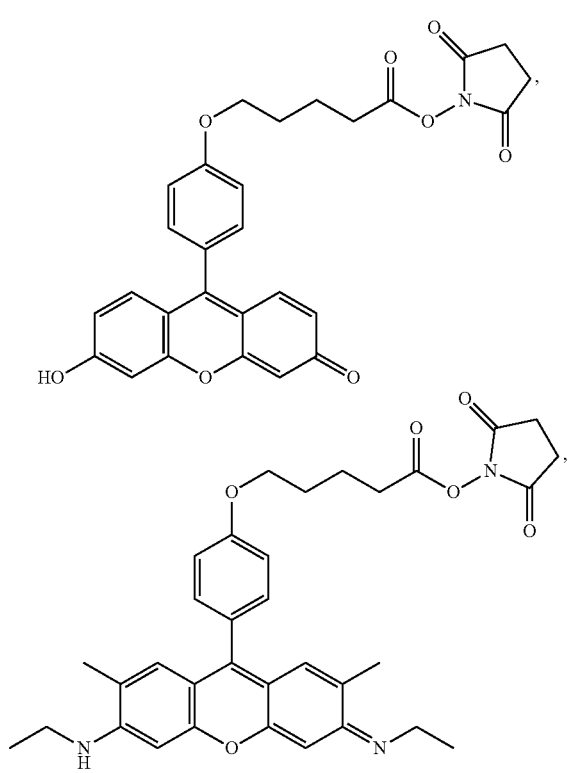

-continued

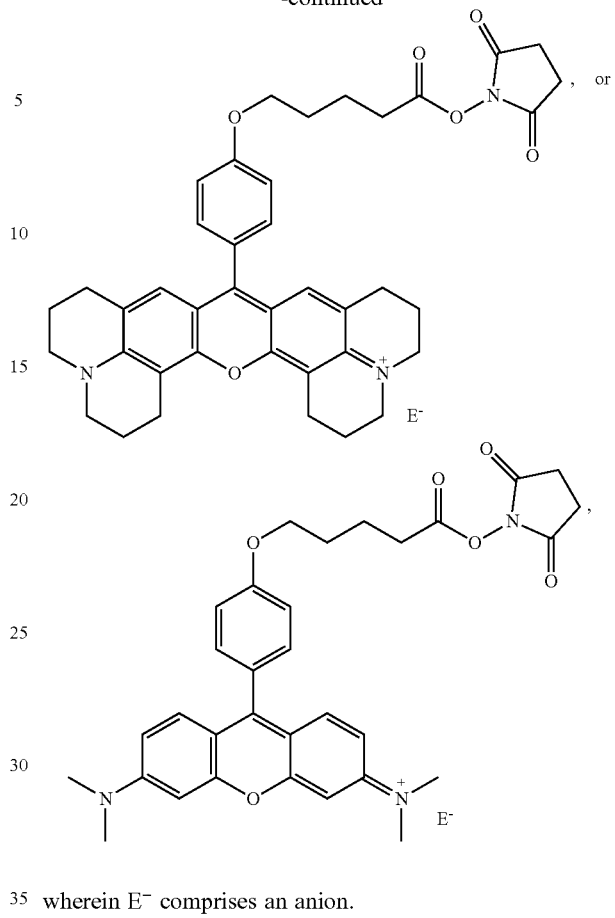

wherein E⁻ comprises an anion.

In some embodiments, any of the compounds described is a fluorescent dye.

Examples 1-16 below describe some of the methods available for synthesizing several of the above dyes. Other methods are known in the art.

For purposes of synthesis of these dyes, reactive thiol, amine or hydroxyl groups can be protected during various synthetic steps and the reactive groups generated after removal of the protective group. Use of a terminal alkene or alkyne groups for attachment of markers is disclosed for example in U.S. Patent Publication 2003/0225247. The use of platinum coordinate groups for attachment of other dyes is disclosed for example in U.S. Pat. No. 5,580,990, and the use of alkyl groups is disclosed for example in U.S. Pat. No. 6,593,465.

In various embodiments, the dyes provided herein further comprise a member of a binding pair, to provide additional binding capabilities. The member of the binding pair can be covalently bound to any portion of the dye. In some of these embodiments, the member of a binding pair is covalently bound to the fluorescent dye through reactive group Z.

Any binding pair now known or later discovered can be utilized in these embodiments. Nonlimiting examples include sugar/lectins, antigen/antibodies, hapten/antibodies, ligand/receptors, hormone/receptors, enzyme/substrates, biotin/avidin, and biotin/streptavidin.

Any one of the dyes of the instant invention can be utilized with another dye to form a fluorescence energy transfer system, where the signal is influenced by Förster resonance energy transfer (also known as fluorescence resonance energy transfer, or FRET). FRET uses two fluorophores (an energy transfer pair) where the emission spectrum of one fluorophore (the donor) is of higher energy (having a shorter wavelength) and overlaps the absorption spectrum of the other fluorophore (the acceptor). When the two fluorophores are brought within about 10-100 Å and the donor fluorophore is excited, the energy of the donor is transferred to the acceptor by a resonance induced dipole-dipole interaction. This interaction is observed by fluorescence quenching of the donor fluorophore and/or emission of the acceptor fluorophore. FRET interactions are utilized with many assays, particularly in molecular biology. See, e.g., U.S. Pat. Nos. 4,868,103; 5,237,515; and 6,117,635, U.S. Patent Publications 2005/0176014 and 2005/0042618, and references cited therein.

Thus, in some embodiments, a fluorescence energy transfer system is provided. The fluorescence energy transfer system comprises any of the above-described fluorescent dyes and a second dye that is capable of energy transfer with the fluorescent dye. Such a system is utilized in Example 19, where PCR amplification of HCV RNA was performed with one HCV primer labeled with Dye 1 (Example 4) as a FRET acceptor and another HCV primer labeled with fluorescein as a FRET donor. The primers are extended in the presence of HCV RNA and the extended primers hybridize, bringing the acceptor and donor dyes together to undergo a FRET interaction.

In various embodiments, any of the fluorescent dyes described above is bound to a target molecule. In some of these embodiments, the dye is covalently bound to the target molecule, e.g., by contacting reactive group Z with the target molecule such that reactive group Z reacts with the target molecule to form a covalent bond between reactive group Z and the target molecule. In other of these embodiments, the dye is noncovalently bound to the target molecule, e.g., through a first member of a binding pair on the target molecule and a second member of the binding pair bound to the fluorescent dye through reactive group Z. This latter case is not narrowly limited to the use of any particular binding pair. Nonlimiting examples of binding pair members that may be utilized here are sugars, lectins, antigens, haptens, antibodies, receptors ligands, hormone ligands, hormone receptors, enzymes, enzyme substrates, biotin, avidin, and streptavidin.

As used herein, a "target molecule" encompasses a moiety that specifically binds to an analyte. Thus, binding between the analyte-specific moiety ("target") and its corresponding analyte may be monitored by essentially determining the presence or amount of dye that is bound to the analyte. Examples of such assays include hybridizations between complementary nucleic acids as well as binding between antibodies and their corresponding antigens. Other binding pairs that may be of interest include but are not limited to ligand/receptor, hormone/hormone receptor, antibody/antigen, carbohydrate/lectin and enzyme/substrate. Assays may be carried out where one component is fixed to a solid support and a corresponding partner is in solution. By binding to the component fixed to the support, the partner becomes attached to the support as well. A well-known example of this method is microarray assays where labeled analytes become bound to discrete sites on the microarray. Homogeneous probe-dependent assays are also well known in the art and may take advantage of the present invention. Examples of such methods are energy transfer between adjacent probes (U.S. Pat. No. 4,868,103), the Taqman exonuclease assay (U.S. Pat. Nos. 5,538,848 and 5,210,015), Molecular Beacons (U.S. Pat. Nos. 5,118,801 and 5,925,517) and various real time assays (U.S. Patent Publication 2005/0137388).

These embodiments can utilize any target molecule now known or later discovered. Examples of useful target molecules to which the dye can be bound include but are not limited to a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, streptavidin, digoxigenin, carbohydrate, oligosaccharide, polysaccharide, lipid, glycolipid, viral particle, viral component, bacterial cell, bacterial component, eukaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof. Where the target is a nucleoside, nucleotide, oligonucleotide, or polynucleotide, such a target can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues or any combination thereof.

The dyes of the present invention may have dyes as targets, thereby creating composite dyes. By joining the dyes of the present invention to another dye, unique properties may be enjoyed that are not present in either dye alone. For instance, if one of the dyes of the present invention is joined to another dye such that it creates an extended conjugation system, the spectral characteristics of the dye may be different than either dye component. Another example of this method is where the conjugation systems do not overlap but the proximity allows an internal energy transfer to take place thereby extending the Stokes shift. See, e.g., U.S. Pat. Nos. 5,401,847; 6,008,373; and 5,800,996. Other properties may also be enhanced by this joining, for example, the joining together of two ethidium bromide molecules generating a dye that has enhanced binding to nucleic acids (U.S. Patent Publication 2003/0225247). Other composite dyes have been described that simultaneously enjoy both properties, i.e. enhanced binding and energy transfer (U.S. Pat. No. 5,646,264). Furthermore, these composite dyes are not limited to binary constructs of only two dyes, but may comprise oligomeric or polymeric dyes. These composite dyes may be comprised of the same dye or different dyes may be joined together depending upon the properties desired.

Antibodies labeled with dyes of the present invention may be used in various formats. For example, an antibody with one of the dyes of the present invention may be used in an immunofluorescent plate assay or in situ analysis of the cellular location and quantity of various antigenic analytes. Antibodies labeled with dyes may also be used free in solution in cell counting or cell sorting methods that use a flow cytometer or for in vitro or in vivo imaging of animal models. The presence or absence of a signal may then be used to indicate the presence or absence of the analyte itself. An example of this is a test where it is sufficient to know whether a particular pathogen is present in a clinical specimen. Quantitative assays may also be carried out where the amount of target is being determined. An example of this is the previously cited microarray assay where the rise or fall in the amount of particular mRNA species may be of interest.

In another embodiment of the present invention, the dyes described above may be attached to a carrier with a more general affinity. Dyes may be attached to intercalators that in themselves do not provide signal generation but by virtue of their binding may bring a dye in proximity to a nucleic acid. A further example is attachment of dyes to SDS molecules thereby allowing dyes to be brought into proximity to proteins. Thus this embodiment describes the adaptation of a dye or dyes that lack affinity to a general class of molecules may be adapted by linking them to non-dye molecules or macromolecules that can convey such properties. Various applications may enjoy the benefits of binding the dyes of the present invention to appropriate targets. As described above, staining of macromolecules in a gel is a methodology that has a long history of use. More recent applications that also may find use are real time detection of amplification (U.S. Pat. Nos. 5,994,056 and 6,174,670, and U.S. Patent Publication 2005/0137388), and binding of nucleic acids to microarrays. In situ assays may also find use where the binding of dyes of the present invention is used to identify the location or quantity of appropriate targets.

The present invention also provides a kit for labeling a target molecule. The kit comprises any of the above-described fluorescent dyes, with additional reagents useful for labeling the target molecule. The target molecule in these embodiments is not narrowly limited to any particular type of compound. Non-limiting examples include a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, streptavidin, digoxigenin, carbohydrate, oligosaccharide, polysaccharide, lipid, glycolipid, viral particle, viral component, bacterial cell, bacterial component, eukaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof. Where the target is a nucleoside, nucleotide, oligonucleotide, or polynucleotide, such a target can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues or any combination thereof. In some of these embodiments, the target molecule is a nucleic acid, a nucleic acid analog, a protein, a peptide, an antibody, an antibody fragment, a carbohydrate, a polysaccharide, an oligosaccharide, a nucleotide, a nucleotide analog, a hapten, or an organic compound less than 2000 daltons. In particularly useful embodiments, the target molecule is a nucleic acid or a protein.

The additional reagents of these kits can include any reagents necessary for labeling any target molecule, such as a buffer, an enzyme, one or both of a binding pair (as described above), chemical reagents to effect the binding of the dye to the target molecule, and/or the target molecule itself. In some embodiments, the kit also includes instructions for labeling the target molecule.

Additionally provided is another kit for labeling a target molecule. The kit in these embodiments comprises a first fluorescent dye and a second fluorescent dye that form an energy transfer pair, wherein the first fluorescent dye is any of the fluorescent dyes described above. In some embodiments, the kit also comprises additional reagents and/or instructions useful for labeling target molecules with the energy transfer pair. The additional reagents of these kits can include any reagents necessary for labeling any target molecule, such as a buffer, an enzyme, one or both of a binding pair (as described above), chemical reagents to effect the binding of the dye to the target molecule, and/or the target molecule itself.

As with the previously described kits, the target molecule in these embodiments is not narrowly limited to any particular type of compound, and could include, e.g., any of the target molecules discussed previously. In some embodiments, the target molecule is a nucleic acid or a protein.

The present invention is also directed to a target molecule labeled with any of the fluorescent dyes described above.

The target molecule in these embodiments is not narrowly limited to any particular type of compound. Non-limiting examples include a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, streptavidin, digoxigenin, carbohydrate, oligosaccharide, polysaccharide, lipid, glycolipid, viral particle, viral component, bacterial cell, bacterial component, eukaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof. Where the target is a nucleoside, nucleotide, oligonucleotide, or polynucleotide, such a target can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues or any combination thereof. In some of these embodiments, the target molecule is a nucleic acid, a nucleic acid analog, a protein, a peptide, an antibody, an antibody fragment, a carbohydrate, a polysaccharide, an oligosaccharide, a nucleotide, a nucleotide analog, a hapten, or an organic compound less than 2000 daltons. In particularly useful embodiments, the target molecule is a nucleic acid or a protein.

In some of these embodiments, the fluorescent dye is covalently bound to the target molecule, for example through reactive group Z.

In other embodiments, the fluorescent dye is noncovalently bound to the target molecule, for example through a binding pair, e.g., where one member of the binding pair is covalently bound to the dye through reactive group Z and the other member of the binding pair is covalently bound to the target, by any means known in the art. The binding pair in these embodiments can be any binding pair now known or later discovered. Nonlimiting examples include a sugar/lectin, an antigen/antibody, a hapten/antibody, a ligand/receptor, a hormone/receptor, an enzyme/substrate, biotin/avidin, or biotin/streptavidin.

In some of these embodiments, the labeled target molecule further comprises a second dye such that the second dye forms an energy transfer pair with the fluorescent dye. Examples of such compositions are well known in the art. See, e.g., U.S. Patent Publication 2005/0137388, describing nucleic acids labeled with both a donor and an acceptor dye.

The labeled target molecule of these embodiments can also be part of a composition that further comprises a second labeled target molecule, where the label on the labeled target molecule and the label on the second labeled target molecule form an energy transfer pair. Examples include two labeled primers, where the two labels form an energy transfer pair, or an antibody labeled with one member of an energy transfer pair and the corresponding antigen labeled with the other member of the energy transfer pair. See, e.g., U.S.

Patent Publication 2005/0137388, PCT Publication WO99/47700 and U.S. Pat. Nos. 5,237,515 and 4,868,103.

In further embodiments, the invention is directed to a method of labeling a target molecule. The method comprises contacting reactive group Z of any of the above-described fluorescent dyes with the target molecule such that reactive group Z reacts with the target molecule to form a covalent bond between reactive group Z and the target molecule.

The target molecule in these embodiments is not narrowly limited to any particular type of compound. Non-limiting examples include a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, streptavidin, digoxigenin, carbohydrate, oligosaccharide, polysaccharide, lipid, glycolipid, viral particle, viral component, bacterial cell, bacterial component, eukaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof. Where the target is a nucleoside, nucleotide, oligonucleotide, or polynucleotide, such a target can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues or any combination thereof. In some of these embodiments, the target molecule is a nucleic acid, a nucleic acid analog, a protein, a peptide, an antibody, an antibody fragment, a carbohydrate, a polysaccharide, an oligosaccharide, a nucleotide, a nucleotide analog, a hapten, or an organic compound less than 2000 daltons. In particularly useful embodiments, the target molecule is a nucleic acid or a protein.

In some of these embodiments, the target molecule further comprises a second dye such that the fluorescent dye and the second dye form an energy transfer pair.

The present invention further provides another method of labeling a target molecule. In these embodiments, the method comprises contacting any of the above-described fluorescent dyes with the target molecule, wherein the target molecule comprises a second member of the binding pair. The dye in these embodiments comprises the first member of the binding pair. As such, when the dye is combined with the target molecule, the first and second members of the binding pair bind together, thus noncovalently labeling the target molecule with the dye.

These embodiments encompass the use of any target molecule now known or later discovered, e.g., as described above. In some embodiments, the target molecule is a nucleic acid, a nucleic acid analog, a protein, a peptide, an antibody, an antibody fragment, a carbohydrate, a polysaccharide, an oligosaccharide, a nucleotide, a nucleotide analog, a hapten, or an organic compound less than 2000 daltons. In particularly useful embodiments, the target molecule is a nucleic acid or a protein, as described above.

As with above-described embodiments, any binding pair now known or later discovered can be utilized for these methods. Nonlimiting examples of useful binding pairs are a sugar/lectin, an antigen/antibody, a hapten/antibody, a ligand/receptor, a hormone/receptor, an enzyme/substrate, biotin/avidin, or biotin/streptavidin.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Synthesis of 7-methoxy-2,2,4-trimethyl-1,2-dihydroquinoline

The compound m-anisidine (26 ml, 0.23 mol) was slowly added to acetic acid (2.6 ml) with stirring, followed by slow addition of mesityl oxide (27 ml, 0.23 mol). After the mixture was stirred at room temperature overnight, concentrated hydrobromic acid (50 ml) was added. The mixture was stirred for an additional hour. The precipitate was then filtered and washed with acetone. The resulting solid was then dissolved in water (100 ml) and neutralized to pH 7 with 10N aqueous sodium hydroxide. The resulting solution was extracted with chloroform (3×50 mL) and dried over anhydrous sodium sulfate. After filtering off the sodium sulfate, the solution was evaporated under vacuum to give crude product, which was recrystalized with hexanes to give a yellowish solid (15.5 g, 33% yield). The structure of 7-methoxy-2,2,4-trimethyl-1,2-dihydroquinoline is:

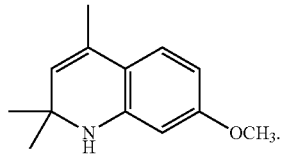

Example 2

Synthesis of 1-ethyl-7-methoxy-2,2,4-trimethyl-1,2-dihydroquinoline

The compound 7-methoxy-2,2,4-trimethyl-1,2-dihydroquinoline (5.0 g, 24.6 mmols) from Example 1 was dissolved in anhydrous DMF (40 ml). Calcium carbonate (3.0 g, 30 mmols) and ethyl iodide (4.7 g, 30 mmols) were subsequently added. The mixture was heated at 120° C. with vigorous stirring for 18 hours. After the mixture was cooled to room temperature, it was poured into water (300 mL). The suspension was filtered through a pad of celite then extracted with chloroform (3×100 mL). The combined chloroform layer was washed with water (3×200 mL) and then dried with anhydrous sodium sulfate. The solvent was evaporated under vacuum to give a dark green oil (5.72 g, 100% yield). The structure of 1-ethyl-7-methoxy-2,2,4-trimethyl-1,2-dihydroquinoline is:

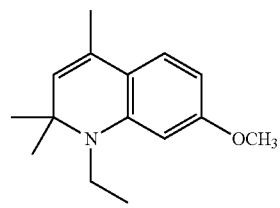 [SMILES: CCN1c2cc(OC)ccc2C(C)=CC1(C)C]

Example 3

Synthesis of 1-ethyl-2,2,4-trimethyl-1,2-dihydroquinolin-7-ol

The compound 1-ethyl-7-methoxy-2,2,4-trimethyl-1,2-dihydroquinoline (5.72 g) from Example 2 was added to a mixture of concentrated hydrobromic acid (13 mL) and glacial acetic acid (13 mL). After the mixture was stirred at reflux for 6 hours, it was cooled with ice and neutralized with 10 N aqueous sodium hydroxide to pH 7. The mixture was then extracted with chloroform (3×50 ml) and dried over anhydrous sodium sulfate, then filtered and evaporated to give a sticky green oil as the crude product (6.02 g), which was used without further purification. The structure of 1-ethyl-2,2,4-trimethyl-1,2-dihydroquinolin-7-ol is given below:

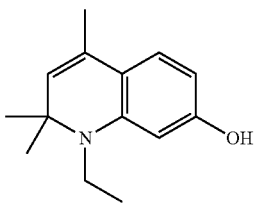 [SMILES: CCN1c2cc(O)ccc2C(C)=CC1(C)C]

Example 4

Synthesis of Dye 1 (EZRed620)

The compounds 1-ethyl-2,2,4-trimethyl-1,2-dihydroquinolin-7-ol (220 mg, 1.0 mmol) (Example 3) and 2-(4-formylphenoxy)acetic acid (61 mg, 0.34 mmol) were mixed thoroughly and heated at 150° C. with vigorous stirring for 15 min in a microwave reactor. After the mixture was cooled to room temperature, methanol (5%) in chloroform (total 5 ml) was added, followed by the addition of tetrachloro-1,4-benzoquinone (25.5 mg, 0.51 mmol). This mixture was stirred at room temperature for 20 min. The solvent was then removed under vacuum and the residue purified by flash chromatography. The solvent was removed to give Dye 1 (shown below) as a dark solid (32.2 mg, yield: 16%). $\lambda_{abs}$=594 nm (in methanol), $\lambda_{em}$=611 nm (in methanol).

Dye 1 (EZRed620)

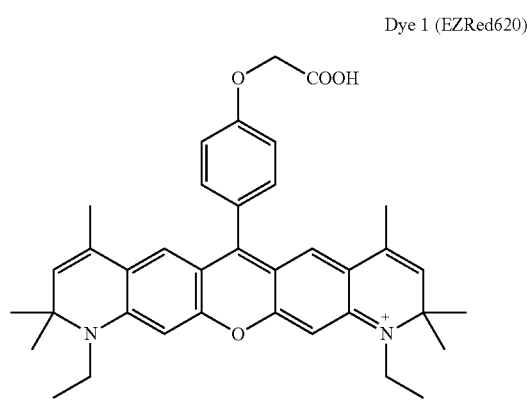

Example 5

Synthesis of Dye 2

Dye 2 (shown below) was prepared using the procedure described in Example 4 except that 1-ethyl-1,2,3,4-tetrahydroquinolin-7-ol substituted for 1-ethyl-2,2,4-trimethyl-1,2-dihydroquinolin-7-ol. Yield: 25%. $\lambda_{abs}$=558 nm (in methanol), $\lambda_{em}$=574 nm (in methanol).

Dye 2

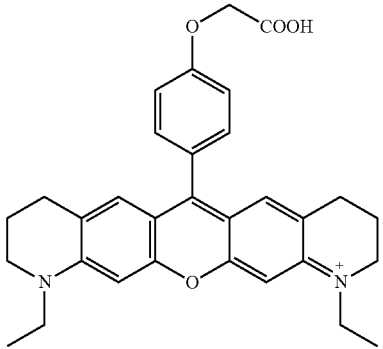

Example 6

Synthesis of 2-(4-(3-hydroxy-6-oxo-6H-xanthen-9-yl)phenoxy)acetic acid (Dye 3)

Dye 3 (shown below) was prepared using the procedure described in Example 4 except that 2-(4-formylphenoxy)acetic acid and resorcinol substituted for 1-ethyl-2,2,4-trimethyl-1,2-dihydroquinolin-7-ol and 2-(4-formylphenoxy)acetic acid. Yield: 34%. $\lambda_{abs}$=485 nm (in methanol), $\lambda_{em}$=511 nm (in methanol).

Dye 3

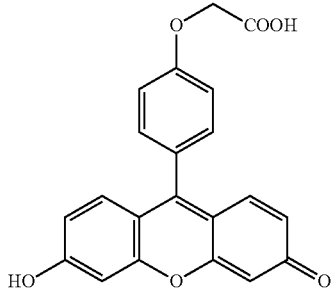

Example 7

Synthesis of 2-(4-(3-(ethylamino)-6-(ethylimino)-2,7-dimethyl-6H-xanthen-9-yl)phenoxy)acetic acid (Dye 4)

Dye 4 (shown below) was prepared using the procedure described in Example 4 except that 3-(ethylamino)-4-methylphenol and 2-(4-formylphenoxy)acetic acid substituted for 1-ethyl-2,2,4-trimethyl-1,2-dihydroquinolin-7-ol and 2-(4-formylphenoxy)acetic acid. Yield: 12%. $\lambda_{abs}$=525 nm (in methanol), $\lambda_{em}$=540 nm (in methanol).

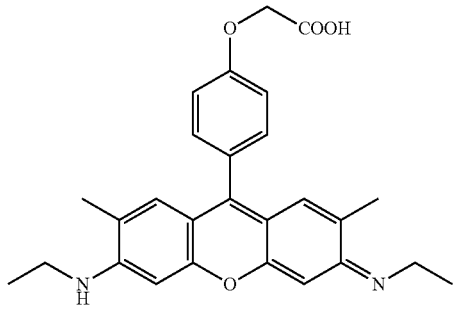

Dye 4

Example 8

Synthesis of Dye 5

Dye 5 (shown below) was prepared using the procedure described in Example 4 except that 2-(4-formylphenoxy) acetic acid and 8-hydroxyjulolidine substituted for 1-ethyl-2,2,4-trimethyl-1,2-dihydroquinolin-7-ol and 2-(4-formylphenoxy)acetic acid. Yield: 22%. $\lambda_{abs}$=570 nm (in methanol), $\lambda_{em}$=584 nm (in methanol).

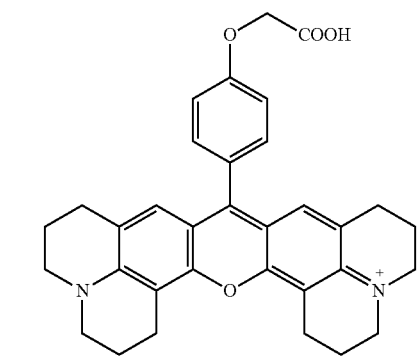

Dye 5

Example 9

Synthesis of N-(9-(4-(carboxymethoxy)phenyl)-6-(dimethylamino)-3H-xanthen-3-ylidene)-N-methyl-methanaminium (Dye 6)

Dye 6 (shown below) was prepared using the procedure described in Example 4 except that 2-(4-formylphenoxy) acetic acid and 3-(dimethylamino)phenol substituted for 1-ethyl-2,2,4-trimethyl-1,2-dihydroquinolin-7-ol and 2-(4-formylphenoxy)acetic acid. Yield: 36%. $\lambda_{abs}$=548 nm (in methanol), $\lambda_{em}$=566 nm (in methanol).

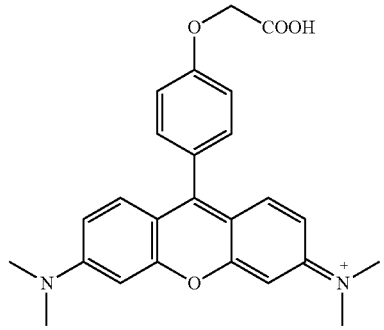

Dye 6

Example 10

Synthesis of 5-(4-formylphenoxy)pentanoic acid

Methyl 5-bromovelerate (13.4 g, 68.6 mmol) and anhydrous potassium carbonate (18.93 g, 137 mmol) was added to a solution of 4-hydroxybenzaldehyde (8.38 g, 68.6 mmol) in anhydrous acetone (140 ml). The mixture was heated at reflux for 16 hours with vigorous stirring. After the mixture was cooled to room temperature and filtered, the solvent was removed under vacuum. The residue was dissolved in dichloromethane (200 mL) and washed sequentially with aqueous sodium hydroxide (1 N, 200 ml), water (200 ml) and brine (200 ml). The solvent was evaporated under vacuum to give a yellowish crystal. The crystal was dissolved in a mixture of THF (200 ml) and hydrochloric acid (6 N, 30 ml). The mixture was then heated to reflux for 3 hours, after which the THF was removed under vacuum. The oil was then extracted with chloroform (4×50 ml). The combined chloroform layer was washed with water (2×150 ml) and brine (200 ml), and then dried with anhydrous sodium sulfate. After the solvent was removed, the acid was obtained as a yellow liquid. The structure of 5-(4-formylphenoxy)pentanoic acid is:

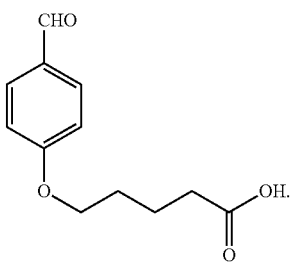 [SMILES: O=Cc1ccc(OCCCCC(=O)O)cc1]

Example 11

Synthesis of Dye 7

Dye 7 (shown below) was prepared using the procedure described in Example 4 except that 5-(4-formylphenoxy) pentanoic acid and 1-ethyl-2,2,4-trimethyl-1,2-dihydroquinolin-7-ol substituted for 1-ethyl-2,2,4-trimethyl-1,2-dihydroquinolin-7-ol and 2-(4-formylphenoxy)acetic acid. Yield: 17%. $\lambda_{abs}$=590 nm (in methanol), $\lambda_{em}$=613 nm (in methanol).

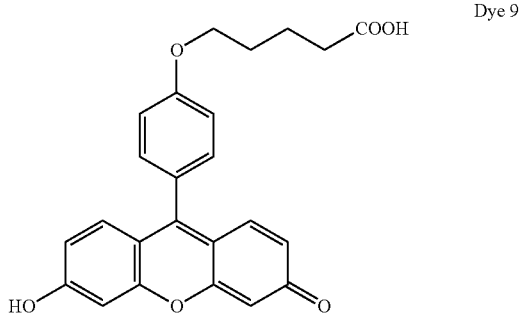 [SMILES: O=C(O)CCCCOc1ccc(-c2c3ccc(=O)cc-3oc3cc(O)ccc23)cc1]

Dye 7

Example 12

Synthesis of Dye 8

Dye 8 (shown below) was prepared using the procedure described in Example 4 except that 5-(4-formylphenoxy)pentanoic acid and 1-ethyl-1,2,3,4-tetrahydroquinolin-7-ol substituted for 1-ethyl-2,2,4-trimethyl-1,2-dihydroquinolin-7-ol and 2-(4-formylphenoxy)acetic acid. Yield: 23%. $\lambda_{abs}$=559 nm (in methanol), $\lambda_{em}$=574 nm (in methanol).

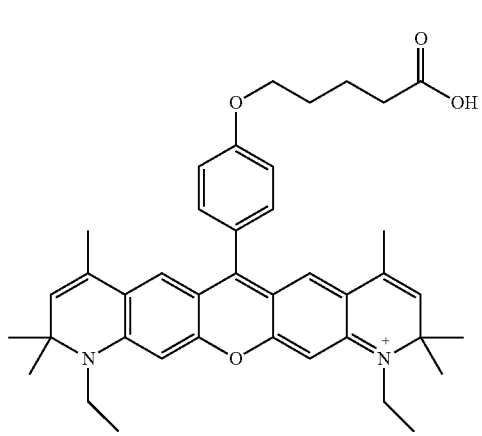

Dye 8

Example 13

Synthesis of 5-(4-(3-hydroxy-6-oxo-6H-xanthen-9-yl)phenoxy)pentanoic acid (Dye 9)

Dye 9 (shown below) was prepared using the procedure described in Example 4 except that 5-(4-formylphenoxy)pentanoic acid and resorcinol substituted for 1-ethyl-2,2,4-trimethyl-1,2-dihydroquinolin-7-ol and 2-(4-formylphenoxy)acetic acid. Yield: 26%. $\lambda_{abs}$=486 nm (in methanol), $\lambda_{em}$=513 nm (in methanol).

Example 14

Synthesis of (Z)-5-(4-(3-(ethylamino)-6-(ethylimino)-2,7-dimethyl-6H-xanthen-9-yl)phenoxy)pentanoic acid (Dye 10)

Dye 10 (shown below) was prepared using the procedure described in Example 4 except that 3-(ethylamino)-4-methylphenol and 5-(4-formylphenoxy)pentanoic acid substituted for 1-ethyl-2,2,4-trimethyl-1,2-dihydroquinolin-7-ol and 2-(4-formylphenoxy)acetic acid. Yield: 17%. $\lambda_{abs}$=524 nm (in methanol), $\lambda_{em}$=541 nm (in methanol).

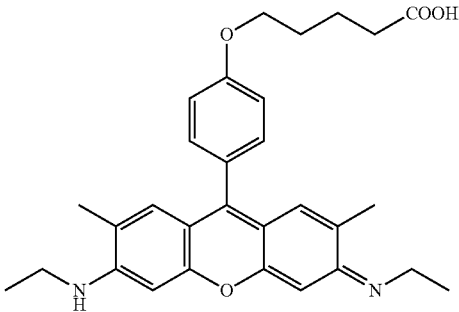

Dye 10

Example 15

Synthesis of Dye 11

Dye 11 (shown below) was prepared using the procedure described in Example 4 except that 5-(4-formylphenoxy)pentanoic acid and 8-hydroxyjulolidine substituted for 1-ethyl-2,2,4-trimethyl-1,2-dihydroquinolin-7-ol and 2-(4-formylphenoxy)acetic acid. Yield: 28%. $\lambda_{abs}$=569 nm (in methanol), $\lambda_{em}$=584 nm (in methanol). The structure of dye 11 is given below:

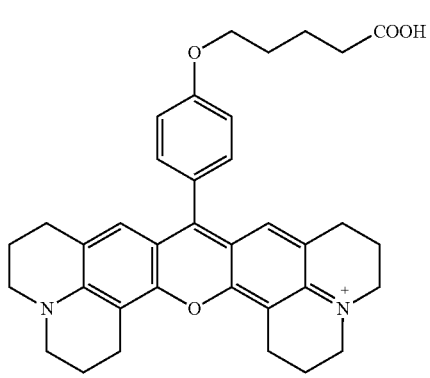

Dye 11

Example 16

Synthesis of N-(9-(4-(4-carboxybutoxy)phenyl)-6-(dimethylamino)-3H-xanthen-3-ylidene)-N-methyl-methanaminium (Dye 12)

Dye 12 (shown below) was prepared using the procedure described in Example 4 except that 5-(4-formylphenoxy)pentanoic acid and 3-(dimethylamino)phenol substituted for 1-ethyl-2,2,4-trimethyl-1,2-dihydroquinolin-7-ol and 2-(4-formylphenoxy)acetic acid. Yield: 23%. $\lambda_{abs}$=547 nm (in methanol), $\lambda_{em}$=565 nm (in methanol). The structure of dye 12 is given below:

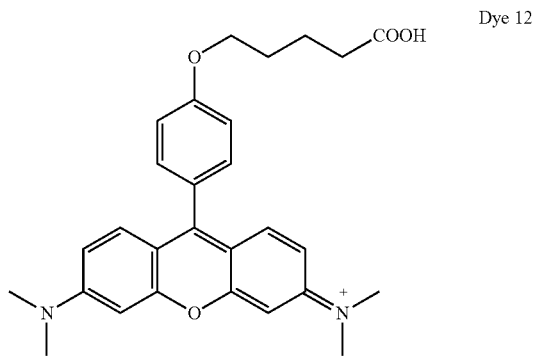

Dye 12

Example 17

Comparison of Spectra of Dye 1 (EZRed620) with Roche LC-Red 640 Dye

Figure 1B:
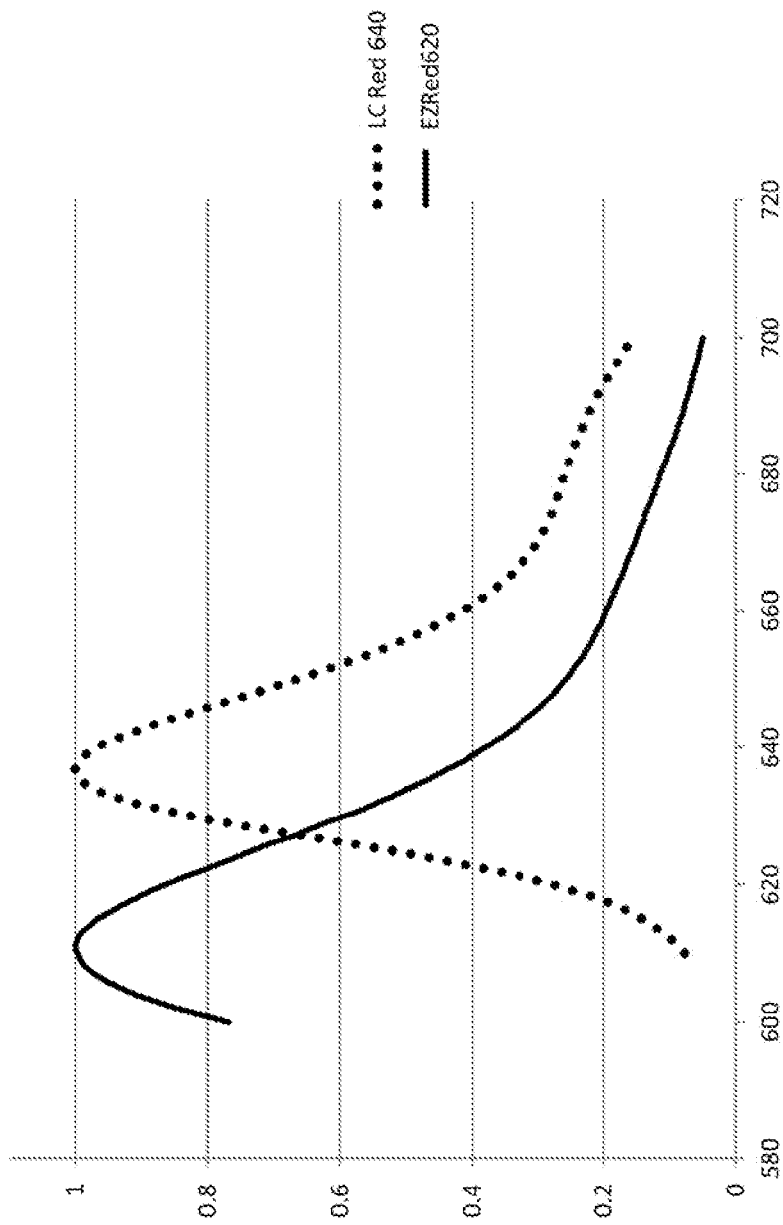
Figure 1C:
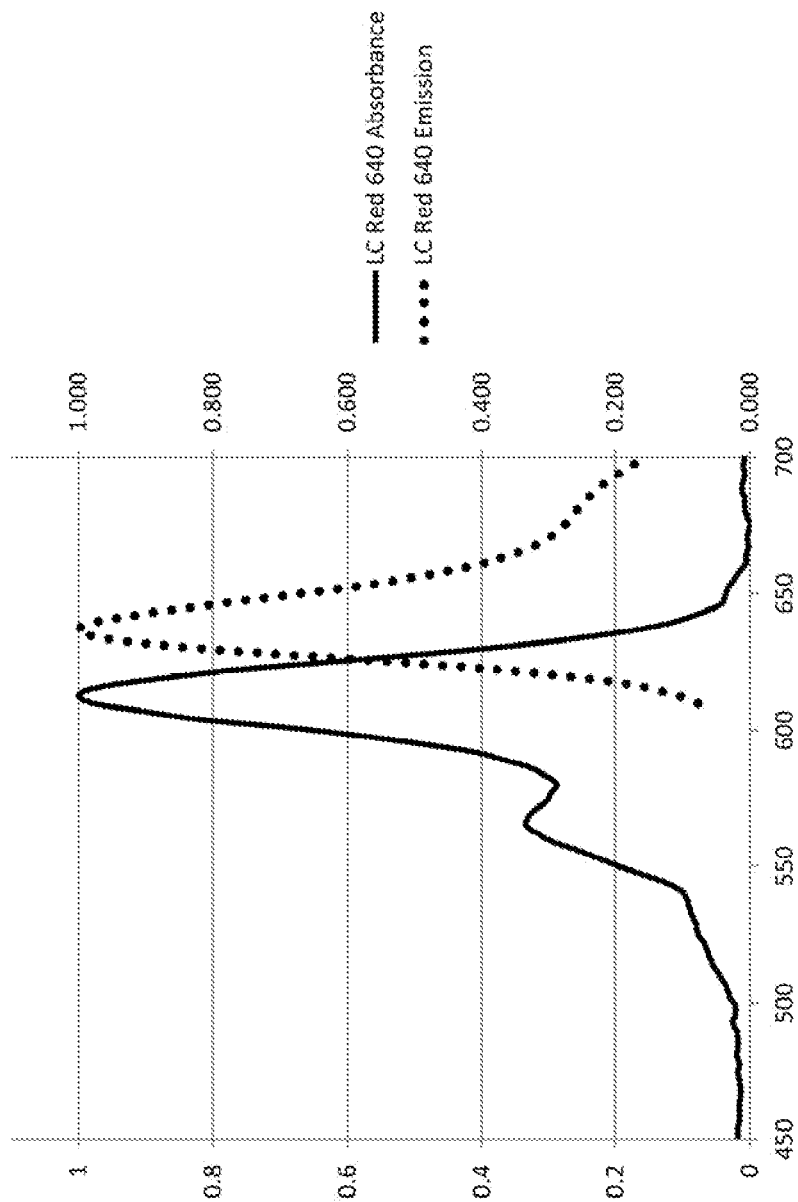
Figure 1D:
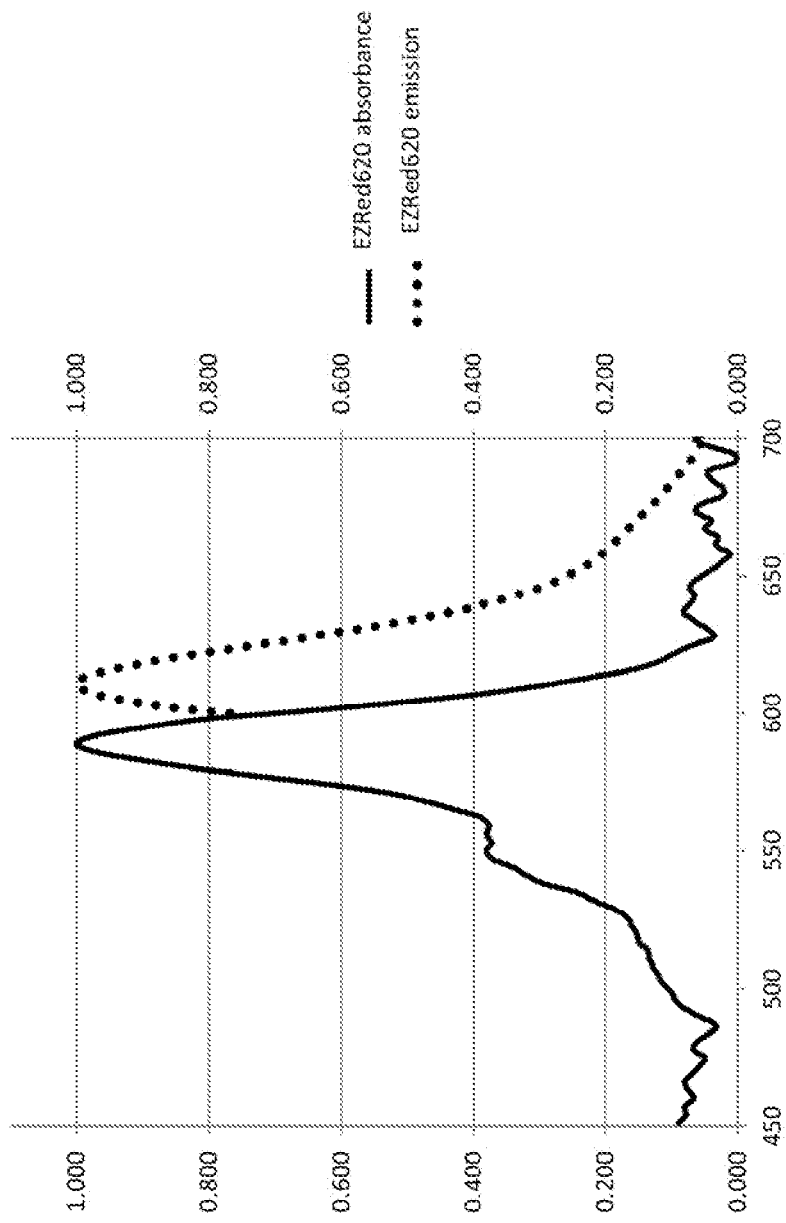

Spectral properties of Dye 1 (Example 4) were determined and compared to Roche LC-Red 640. The UV-Vis spectra of EZRed620 and LC Red 640 were recorded in methanol with a NanoDrop® ND-1000 Spectrophotometer. The wavelengths of maximum absorption of EZRed620 and LC Red 640 were at 589 nm and 613 nm, respectively. The fluorescence spectra were recorded in methanol with Photo Technology International (PTI) fluorometer. The maximum emission wavelengths of EZRed620 and LC Red 640 were 611 nm and 637 nm under these conditions, respectively. Graphs of the results of these studies are shown in FIGS. 1A-1D.

Example 18

Bioconjugation of Dye 1 to Oligonucleotide

Dye 1 (2 μmol) was dissolved in amine-free DMF (140 μl), followed by the addition of 2-succinimido-1,1,3,3-tetramethyluronium tetrafluoroborate (2.4 μmols) and diisopropylethylamine (4.4 μmols). The mixture was stirred at room temperature for 30 min, and then added to a solution of oligonucleotide containing an amine linker (80 nmols) in 0.9 M sodium borate buffer (320 μL, pH 8.5). The mixture was stirred at room temperature for 16 h. The solvent was removed under vacuum and the residue pellet was purified by HPLC using a gradient of triethylammoniumacetate (0.1 M, pH 6.9) and acetonitrile as eluting solvents. The fractions containing pure conjugates were combined and evaporated, and then coevaporated with water to remove excessive salt. The final blue pellet was dissolve in water and stored at −20° C.

Example 19

HCV Test with Dye 1 (EZRed620)

RNA was isolated from 400 μl plasma or serum from each sample using a QIAamp MinElute Virus Spin Kit in a QIAcube system (QIAGEN, Valencia CA) according to the manufacturer's protocol. The resulting RNA was eluted in 50 μl elution buffer. Five μl of the eluate was subjected to RT-PCR to amplify the HCV target sequence GAGGAAC-UACUGUCUUCACGCAGAAAGCGUCUAGC-CAUGGCGUUAGUAUGAGUG UCG (SEQ ID NO:1). The PCR forward primer was GAGGAACTACTGTCTT-CACGCAGAAAGCG (SEQ ID NO:2); the reverse primer was CGACACTCATACTAACGCCATGGCTAG (SEQ ID NO:3). The forward primer was labeled on the underlined/bolded C with Dye 1 (EZRed620) as a FRET acceptor; the reverse primer was labeled on the underlined/bolded T with fluorescein as a FRET donor. Reverse transcription and PCR amplification was carried out in either a Roche Light Cycler or a Qiagen Rotor-Gene Q RealTime PCR machine. Reverse transcription was performed at 50° C. for 30 min. PCR amplification was conducted at 95° C. for 15 sec to denature and 66° C. for 60 sec. for annealing/extension, with a total of 50 or 60 cycles. RealTime RT-PCR progress was monitored through measuring the strength of the EZRed620 signal. When the Roche Light Cycler system was used, Channel F2 was chosen to measure the EZRed620 signal; when the Qiagen Rotor-gene Q system was used, 470 nm was used for excitation and either 610 nm or 660 nm was used to measure the EZRed620 emission.

Comparison of EZRed620/Rotor-Gene Q with LCRed640/COBAS AmpliPrep for Determination of HCV Viral Load in Clinical Samples Sixty samples, numbered 101 to 160, were tested as positive using the Roche COBAS AmpliPrep. Those samples were subsequently tested using (a) the EZRed620/Rotor-Gene Q system as described above and (b) the LCRed640/COBAS system as per the manufacturer's instructions. Four additional samples, numbered 201 to 204, were also tested. Sample 204 was tested negative with both platforms. All samples were run with negative control samples of water or elution buffer and a known positive sample. Results of the HCV viral load determination for the above-described samples using both platforms is provided in Table 1. The covariance between the EZRed620/Rotor-Gene Q system and the LCRed640/COBAS system was 1.077, r=0.95. This shows that the EZRed620/Rotor-Gene Q system can reliably substitute for the LCRed640/COBAS system with similar results.

TABLE 1

Comparison of RT-PCR HIV viral load determination using two systems.

| Sample # | EZRed620 Rotor-Gene $\log_{10}$ | LCRed640 COBAS $\log_{10}$ |
|---|---|---|
| 101 | 6.55 | 6.62 |
| 102 | 6.36 | 6.02 |
| 103 | 5.14 | 5.06 |
| 104 | 6.22 | 6.43 |
| 105 | 6.02 | 5.29 |
| 106 | 6.37 | 6.85 |
| 107 | 6.21 | 5.94 |
| 108 | 6.49 | 6.25 |
| 109 | 6.29 | 6.10 |
| 110 | 6.35 | 5.68 |
| 121 | 4.41 | 3.84 |
| 122 | 6.35 | 6.71 |
| 123 | 2.67 | 2.02 |
| 124 | 4.85 | 4.29 |
| 125 | 7.09 | 7.58 |
| 126 | 4.40 | 4.94 |
| 127 | 6.26 | 6.36 |
| 128 | 6.02 | 5.80 |
| 129 | 6.30 | 6.92 |
| 130 | 5.08 | 4.81 |
| 131 | 5.76 | 5.48 |
| 132 | 5.36 | 4.99 |
| 133 | 6.08 | 5.85 |
| 134 | 6.83 | 7.26 |
| 135 | 6.73 | 6.88 |
| 136 | 6.78 | 7.61 |
| 137 | 6.02 | 6.03 |
| 138 | 6.54 | 6.96 |
| 139 | 6.54 | 6.86 |
| 140 | 5.34 | 5.23 |
| 141 | 4.37 | 4.83 |
| 142 | 2.86 | 3.22 |
| 143 | 5.59 | 5.12 |
| 144 | 6.23 | 5.91 |
| 145 | 5.59 | 4.95 |
| 146 | 6.34 | 6.22 |
| 147 | 5.62 | 5.64 |
| 148 | 7.02 | 6.95 |
| 149 | 6.76 | 6.56 |
| 150 | 6.95 | 6.85 |
| 151 | 6.60 | 7.01 |
| 152 | 5.53 | 5.25 |
| 153 | 6.60 | 6.60 |
| 154 | 6.46 | 6.24 |
| 155 | 6.61 | 6.42 |
| 156 | 6.05 | 6.06 |
| 157 | 6.81 | 6.73 |
| 158 | 5.62 | 5.40 |
| 159 | 5.03 | 4.96 |
| 160 | 6.84 | 7.45 |
| 201 | 6.31 | 6.26 |
| 202 | 5.56 | 5.40 |
| 203 | 3.12 | 3.02 |

REFERENCES

Ernst, et al. (1989) Cytometry 10:3-10.
Mujumdar, et al. (1989) Cytometry 10:11-19.
Mujumdar et al. (1993) Bioconjugate Chemistry 4:105-111.
Southwick, et al. (1990) Cytometry 11:4187-430.
Zhu et al. (1994) Nucl. Acid Res. 22:3418-3422.
European Patent Publication 0 070 685.
European Patent Publication 0 543 333.
European Patent Publication 0 567 622.
European Patent Publication 0 971 039.
PCT Publication WO99/47700.
PCT Publication WO 99/28500.
U.S. Pat. No. 4,683,202.
U.S. Pat. No. 4,711,955.
U.S. Pat. No. 4,868,103.
U.S. Pat. No. 4,952,685.
U.S. Pat. No. 5,013,831.
U.S. Pat. No. 5,047,519.
U.S. Pat. No. 5,118,801.
U.S. Pat. No. 5,130,238.
U.S. Pat. No. 5,210,015.
U.S. Pat. No. 5,237,515.
U.S. Pat. No. 5,241,060.
U.S. Pat. No. 5,268,486.
U.S. Pat. No. 5,270,184.
U.S. Pat. No. 5,401,847.
U.S. Pat. No. 5,455,166.
U.S. Pat. No. 5,455,175.
U.S. Pat. No. 5,494,810.
U.S. Pat. No. 5,538,848.
U.S. Pat. No. 5,580,990.
U.S. Pat. No. 5,627,027.
U.S. Pat. No. 5,646,264.
U.S. Pat. No. 5,800,996.
U.S. Pat. No. 5,866,336.
U.S. Pat. No. 5,925,517.
U.S. Pat. No. 5,948,648.
U.S. Pat. No. 5,994,056.
U.S. Pat. No. 6,004,286.
U.S. Pat. No. 6,008,373.
U.S. Pat. No. 6,110,630.
U.S. Pat. No. 6,114,350.
U.S. Pat. No. 6,117,635.
U.S. Pat. No. 6,174,670.
U.S. Pat. No. 6,184,379.
U.S. Pat. No. 6,323,337.
U.S. Pat. No. 6,552,199.
U.S. Pat. No. 6,593,465.
U.S. Pat. No. 6,743,605.
U.S. Patent Publication 2003/0225247.
U.S. Patent Publication 2005/0137388
U.S. Patent Publication 2005/0176014.
U.S. Patent Publication 2005/0042618.
U.S. Patent Publication 2003/0225247.
U.S. Patent Publication 2005/0137388.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method for fluorescently labeling a target molecule, comprising the steps of: providing a fluorescent dye compound having the formula:

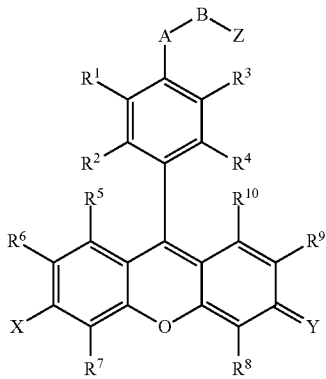

wherein $R^1$, $R^2$, $R^3$, $R^4$, $R^5$, $R^6$, $R^7$, $R^8$, $R^9$, and $R^{10}$ are independently H, F, Cl, Br, I, CN, nitro, azido, hydroxyl, amino, hydrazino, (substituted) aryl, (substituted) aryloxy, alkenyl, alkynyl, alkyl, alkoxy, alkylamino, dialkylamino, arylamino, diarylamino, alkyl(aryl)amino, alkanoylamino, alkylthio, alkylcarbonyl, aryl carbonyl, alkylthiocarbonyl, arylthiocarbonyl, alkyloxycarbonyl, aroxycarbonyl, alkylaminocarbonyl, arylaminocarbonyl, dialkylaminocarbonyl, diarylaminocarbonyl, alkyl(aryl)aminocarbonyl, arylcarboxamido, or Q, the alkyl or alkoxy portions of which are saturated or unsaturated, linear or branched, unsubstituted or further substituted by F, Cl, Br, I, CN, OH, alkenyl, alkynyl, alkylcarbonyl, amide, thioamide, or Q;

wherein Q is selected from the group consisting of a carboxyl group ($CO_2^-$), a carbonate ester ($COER^{11}$), a sulfonate ester ($SO_2ER^{11}$), a sulfoxide ($SOR^{11}$), a sulfone ($SO_2CR^{11}R^{12}R^{13}$), a sulfonamide ($SO_2NR^{11}R^{12}$), a phosphate ($PO_4^=$), a phosphate monoester ($PO_3^-ER^{11}$), a phosphate diester ($PO_2ER^{11}ER^{12}$), a phosphonate ($PO_3^=$), a phosphonate monoester ($PO_2^-ER^{11}$) a phosphonate diester ($POER^{11}ER^{12}$), a thiophosphate ($PSO_3^=$), a thiophosphate monoester ($PSO_2^-ER^{11}$), a thiophosphate diester ($PSOER^{11}ER^{12}$), a thiophosphonate ($PSO_2^=$), a thiophosphonate monoester ($PSO^-ER^{11}$), a thiophosphonate diester ($PSER^{11}ER^{12}$), a phosphonamide ($PONR^{11}R^{12}NR^{14}R^{15}$), a phosphonamide thioanalogue ($PSNR^{11}R^{12}NR^{14}R^{15}$), a phosphoramide ($PONR^{11}R^{12}NR^{13}NR^{14}R^{15}$), a phosphoramide thioanalogue ($PSNR^{11}R^{12}NR^{13}NR^{14}R^{15}S$), a phosphoramidite ($PO_2R^{14}NR^{11}R^{12}$), and a phosphoramidite thioanalogue ($POSR^{14}NR^{11}R^{12}$), wherein E can independently be O or S, and wherein the aryl portions of any of the above are optionally substituted by F, Cl, Br, I, CN, OH, alkenyl, alkynyl, alkylcarbonyl, amide, or thioamide;

wherein $R^1$ in combination with $R^2$, $R^3$ in combination with $R^4$, $R^5$ in combination with $R^6$, or $R^9$ in combination with $R^{10}$ can independently form a 5-10 member ring structure which is saturated or unsaturated, and which is optionally further substituted with an alkyl, an aryl, an alkenyl, an alkynyl, an alkoxy, an aryloxy, a hydroxyl, F, Cl, Br, I, CN, a nitro, an alkylsulfonyl, an arylsulfonyl, an alkylsulfinyl, an arylsulfinyl, a (thio)carbonyl, a (thio)carboxylic acid, a (thio)carboxylic acid ester, a nitro, an amino, a (thio)amide, an azido, a hydrazino, or a (thio)phosphonate where each alkyl group or alkoxy group is independently saturated or unsaturated, linear or branched, or substituted or unsubstituted and each aryl group wherein is independently optionally substituted with F, Cl, Br, I, CN, OH, an alkyl, an alkenyl, an alkynyl, an alkoxy, an aryoxy, an alkylthio, an arylthio, a nitro, an azido, a hydrazino, a carboxyl, a thiocarboxyl, a carbonyl, a thiocarbonyl, a carboxylic acid ester, a thiocarboxylic acid ester, or an amino, amide, thioamide, or Q;

$R^{11}$, $R^{12}$, $R^{13}$, $R^{14}$ and $R^{15}$ are independently hydrogen, a halogen, an amino group, an alkyl group wherein said alkyl group is saturated or unsaturated, linear or branched, or substituted or unsubstituted, an alkoxy group wherein said alkoxy group is saturated or unsaturated, branched or linear, or substituted or unsubstituted, an aryl group wherein said aryl group is unsubstituted or substituted; wherein $R^{11}$ in combination with $R^{12}$, $R^{14}$ in combination with $R^{15}$, $R^{11}$ in combination with $R^{13}$, $R^{11}$ in combination with $R^{14}$, $R^{12}$ in combination with $R^{15}$, or $R^{13}$ in combination with $R^{14}$ can independently form a 5-10 member ring;

X is O, $OR^{16}$, $NR^{17}R^{18}$ or $N^+R^{17}R^{18}$; Y is O, $OR^{16}$, $NR^{19}R^{20}$ or $N^+R^{19}R^{20}$, wherein $R^{16}$, $R^{17}$, $R^{18}$, $R^{19}$ and $R^{20}$ are independently H, alkyl, alkenyl, alkynyl, or aryl; or $R^{17}$ in combination with $R^{18}$, or $R^{19}$ in combination with $R^{20}$ can independently form a 5-10 member ring structure which is optionally further substituted with alkyl, alkenyl, alkynyl, aryl, alkoxy, F, Cl, Br, I, carboxylic acid or carboxylic acid ester, where the alkyl group is saturated or unsaturated, linear or branched, and is optionally further substituted by F, Cl, Br, I, CN, OH, alkenyl, alkynyl, nitro, azido, hydrazino, alkoxy, aryoxy, alkylthio, arylthio, thiocarboxyl, carbonyl, thiocarbonyl, thiocarboxylic acid ester, amino, amide, thioamide, or Q, and the aryl group wherein is optionally substituted by F, Cl, Br, I, CN, OH, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, amino, amide, thioamide, or Q; wherein $R^{17}$ in combination with $R^6$, $R^{18}$ in combination with $R^7$, $R^{19}$ in combination with $R^8$, and $R^{20}$ in combination with $R^9$, can independently form a 5- to 10-member ring structure that is saturated or unsaturated and optionally further substituted with an alkyl, an aryl, an alkenyl, an alkynyl, an alkoxy, an aryloxy, a hydroxyl, F, Cl, Br, I, CN, a nitro, a carbonyl, a thiocarbonyl, a thiocarboxylic acid, a thiocarboxylic acid ester, a nitro, an amino, a (thio)amide, an azido, a hydrazino, or Q, wherein the alkyl group herein is saturated or unsaturated, linear or branched, substituted or unsubstituted, an alkoxy group wherein the alkoxy group is saturated or unsaturated, branched or linear, substituted or unsubstituted; and wherein the aryl group is optionally substituted with F, Cl, Br, I, CN, OH, alkenyl, alkynyl, alkoxy, aryoxy, alkylthio, arylthio, nitro, azido, hydrazino, carboxyl, thiocarboxyl, carbonyl, thiocarbonyl, carboxylic acid ester, thiocarboxylic acid ester, amino, amide, thioamide, or Q;

A is O, S or $NR^{21}$, wherein $R^{21}$ is a hydrogen, an alkyl, an aryl, an alkenyl, an alkynyl, an alkylcarbonyl, an arylcarbonyl, an alkylaminocarbonyl, or an arylaminocarbonyl, the alkyl or aryl portions of which is optionally substituted by an alkyl, an aryl, an alkenyl, an alkynyl, F, Cl, Br, I, CN, OH, an alkoxy, an aryoxy, an alkylthio, an arylthio, a nitro, an azido, a hydrazino, a thiocarboxyl, a carbonyl, a thiocarbonyl, a thiocarboxylic acid ester, or an amino, amide, thioamide, or Q;

B is an alkyl, an alkenyl, an alkynyl, or an aryl linker, the alkyl or aryl portions of which is optionally substituted by an alkyl, an alkenyl, an alkynyl, an aryl, F, Cl, Br, I, CN, OH, an alkoxy, an aryoxy, an alkylthio, an arylthio, a nitro, an azido, a hydrazino, a carboxyl, a thiocarboxyl, a carbonyl, a thiocarbonyl, a carboxylic acid ester, a thiocarboxylic acid ester, or an amino, amide, thioamide, or Q; or B in combination with A form an amide, a thioamide, a carboxylic acid ester, a carboxylic acid thioester, a thiocarboxylic acid ester, an imine, a hyrazone, or Q; and Z is a reactive group selected from the group consisting of an isocyanate, an isothiocyanate, a monochlorotriazine, a dichlorotriazine, a 4,6-dichloro-1,3,5-triazines, a mono- or di-halogen substituted pyridine, a mono- or di-halogen substituted diazine, a maleimide, a haloacetamide, an aziridine, a sulfonyl halide, a carboxylic acid, an acid halide, a phosphonyl halide, a phosphoramidite ($PO_2R^{14}NR^{11}R^{12}$), a phosphoramidite thioanalogue ($POSR^{14}NR^{11}R^{12}$), a hydroxysuccinimide ester, a hydroxysulfosuccinimide ester, an imido ester, an azido, a nitrophenol ester, an azide, a 3-(2-pyridyl dithio)-propionamide, a glyoxal, an aldehyde, a thiol, an amine, a hydrazine, a hydroxyl, a terminal alkene, a terminal alkyne, a platinum coordinate group and an alkylating agent, wherein the carbon lengths for said alkenyl, alkynyl, and alkyl groups are in the range of 1 to 16;

providing a target molecule to be labeled, wherein the target molecule is a peptide or a protein, and;

contacting the fluorescent dye compound with the target molecule such that reactive group Z reacts with the target molecule to form a covalent bond between reactive group Z and the target molecule.

2. The method of claim 1, wherein -A-B—Z is

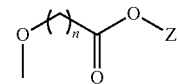

wherein n is 1-10.

3. The method of claim 2, wherein n is 1-4.

4. The method of claim 2, wherein -A-B—Z is

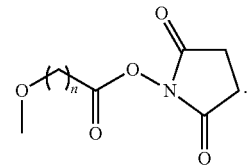

5. The method of claim 1, wherein -A-B—Z is

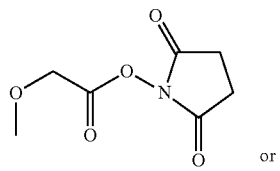

or

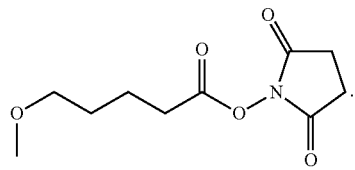

6. The method of claim 1, wherein the fluorescent dye compound has the structure

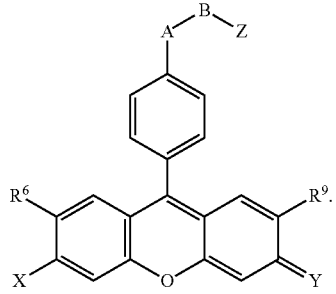

7. The method of claim 6, wherein $R^6$ and $R^9$ are both H or $CH_3$.

8. The method of claim 6, wherein X and Y are
   (a) OH and O, respectively;
   (b) $NHCH_2CH_3$ and $NCH_2CH_3$, respectively; or
   (c) $N(CH_3)_2$ and $N^+(CH_3)_2$, respectively.

9. The method of claim 1, wherein the fluorescent dye compound is selected from the group consisting of:

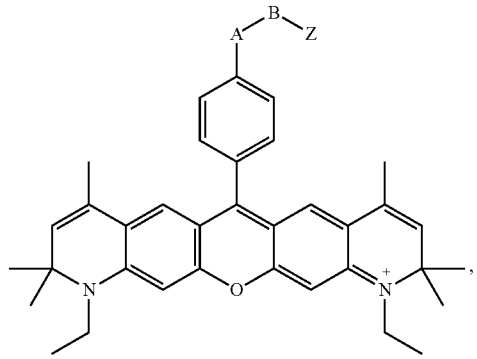

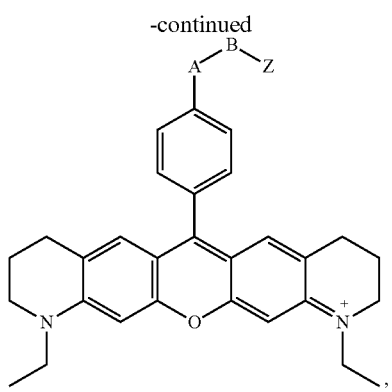

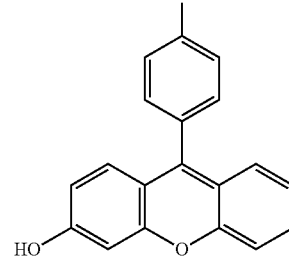

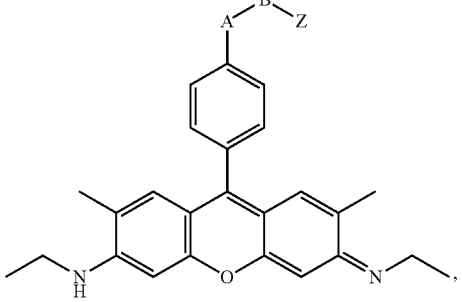

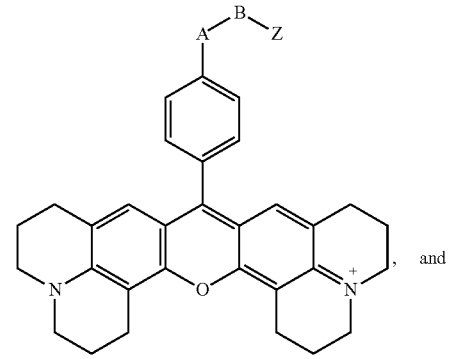

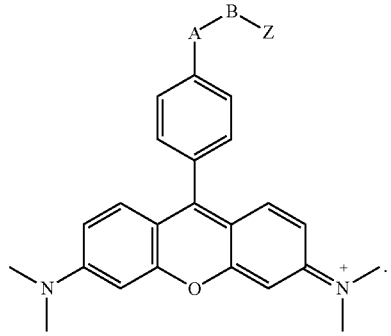

10. The method of claim 9, wherein the fluorescent dye compound is selected from the group consisting of:

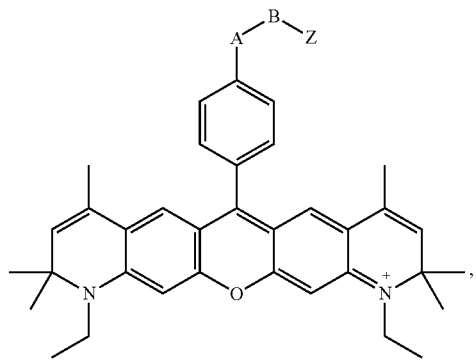
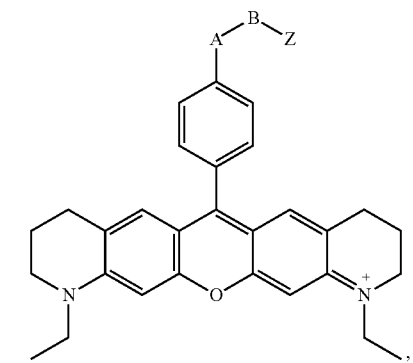
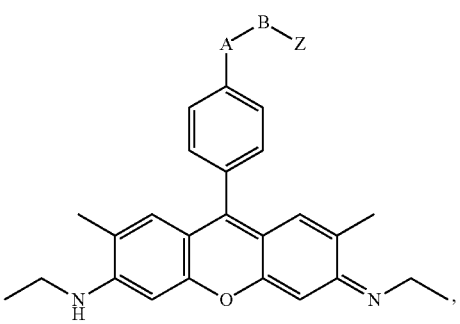
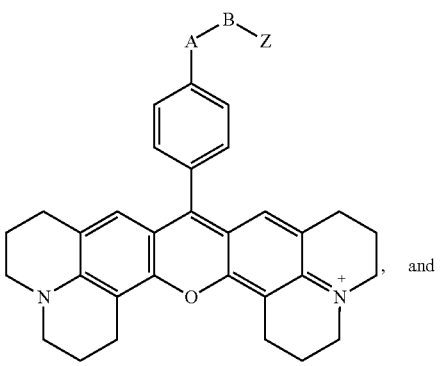
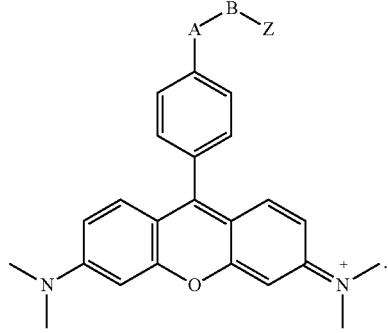
11. The method of claim 1, wherein the fluorescent dye compound is selected from the group consisting of:
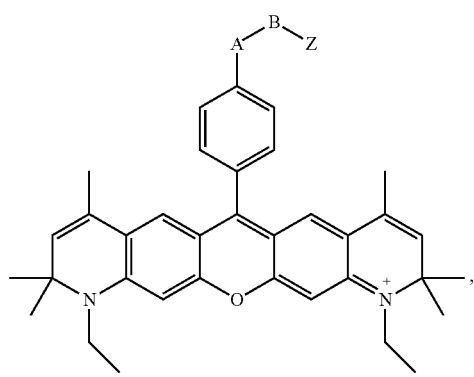
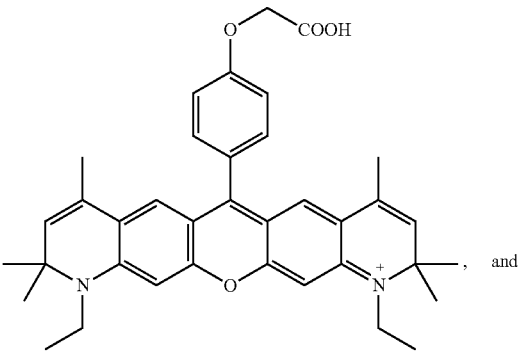, and
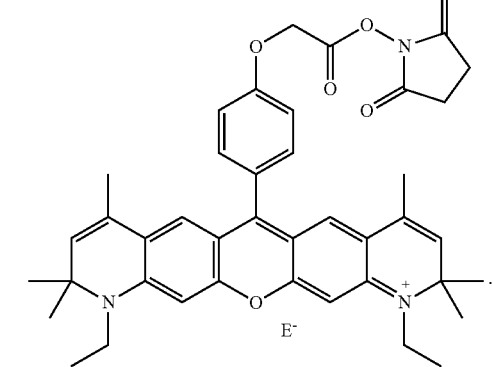
12. The method of claim 1, wherein the fluorescent dye compound is selected from the group consisting of:

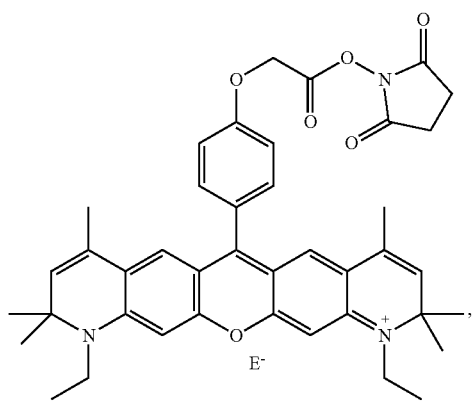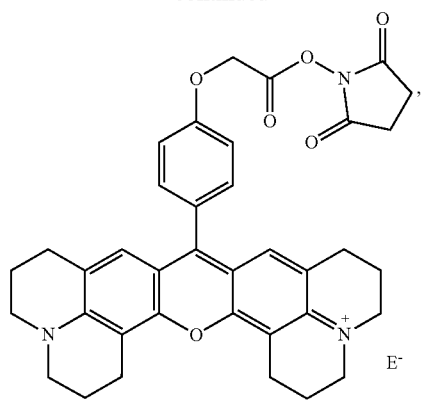
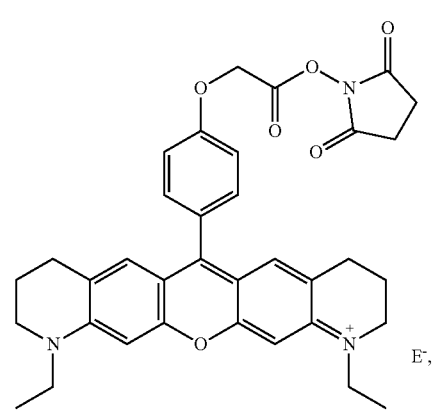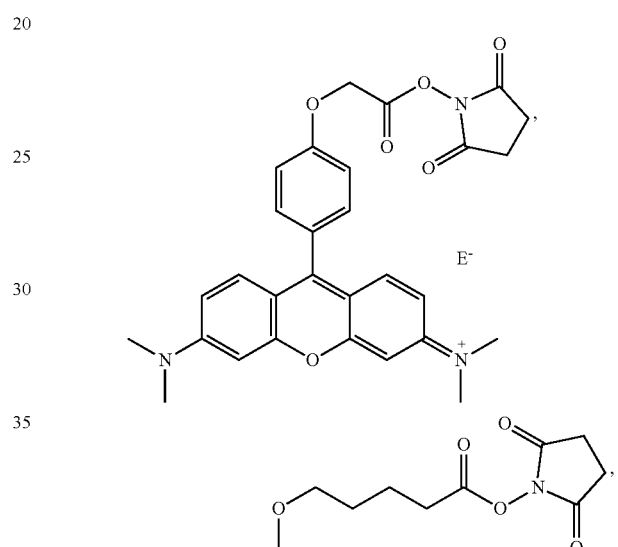
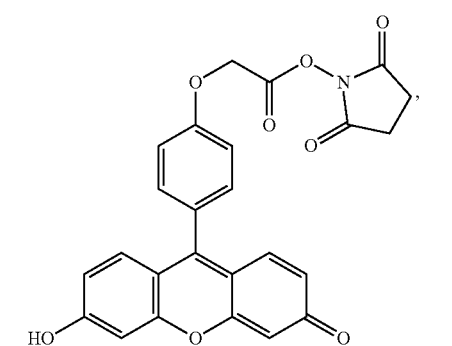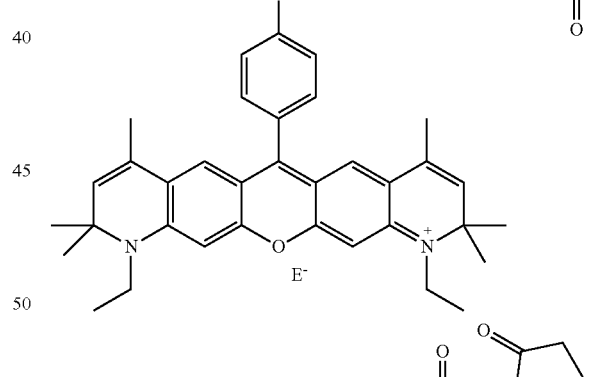
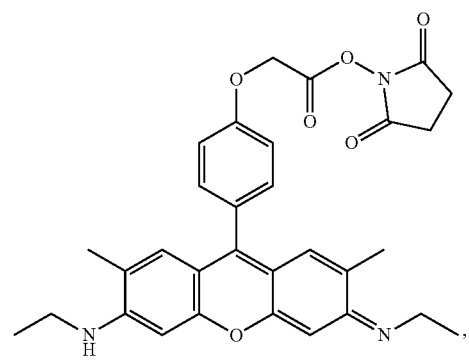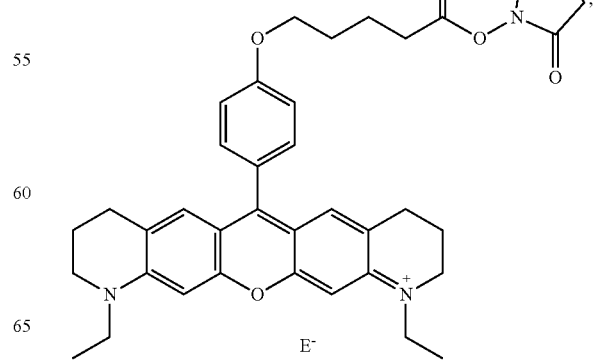

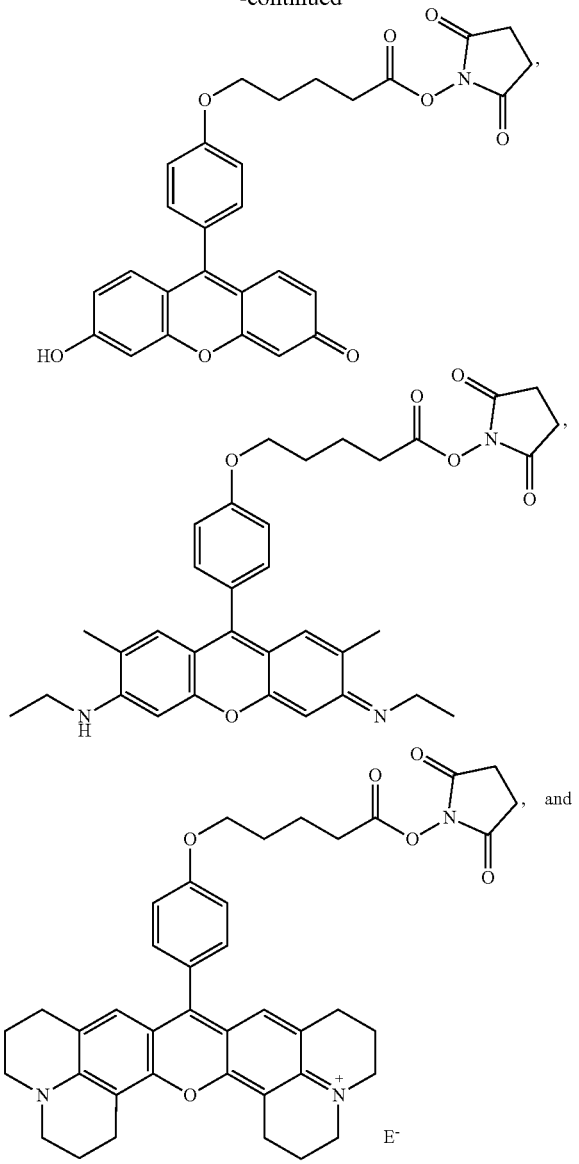

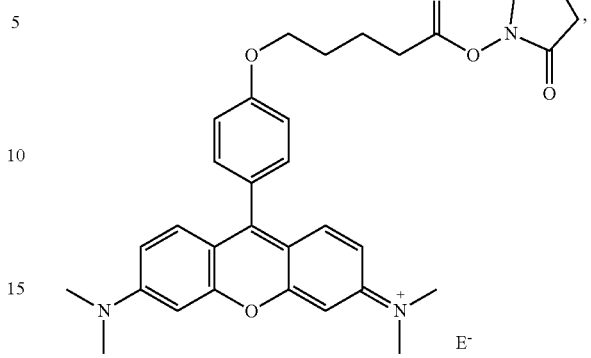

wherein E⁻ is an anion.

13. The method of claim 1, wherein the target molecule is a peptide.

14. The method of claim 1, wherein the target molecule is a protein.

15. The method of claim 14, wherein the target molecule is an antibody or an antibody fragment.

16. The method of claim 9, wherein the target molecule is an antibody or an antibody fragment.

17. The method of claim 12, wherein the target molecule is an antibody or an antibody fragment.

18. The method of claim 1, wherein the carbon lengths for said alkenyl, alkynyl, and alkyl groups are in the range of 1 to 10.

19. The method of claim 13, wherein the carbon lengths for said alkenyl, alkynyl, and alkyl groups are in the range of 1 to 10.

20. The method of claim 14, wherein the carbon lengths for said alkenyl, alkynyl, and alkyl groups are in the range of 1 to 10.

* * * * *